US012741975B2

(12) United States Patent
Chen et al.

(10) Patent No.: US 12,741,975 B2
(45) Date of Patent: Sep. 22, 2026

(54) FUSED POLYCYCLIC SUBSTITUTED 5-CARBOXYLIC ACID THIENOPYRIMIDINE DIONE COMPOUND AND USE THEREOF

(71) Applicant: CMS RESEARCH & DEVELOPMENT PTE. LTD., Singapore (SG)

(72) Inventors: Kevin Chen, Shanghai (CN); Boyu Hu, Shanghai (CN); Kai Zhou, Shanghai (CN); Zhaoguo Chen, Shanghai (CN); Bin Liu, Shanghai (CN); Guoping Hu, Shanghai (CN); Jian Li, Shanghai (CN); Shuhui Chen, Shanghai (CN)

(73) Assignee: CMS RESEARCH & DEVELOPMENT PTE. LTD., Singapore (SG)

( * ) Notice: Subject to any disclaimer, the term of this patent is extended or adjusted under 35 U.S.C. 154(b) by 368 days.

(21) Appl. No.: 18/278,363

(22) PCT Filed: Feb. 21, 2022

(86) PCT No.: PCT/CN2022/077112

§ 371 (c)(1),
(2) Date: Aug. 22, 2023

(87) PCT Pub. No.: WO2022/179476

PCT Pub. Date: Sep. 1, 2022

(65) Prior Publication Data

US 2024/0158413 A1 May 16, 2024

(30) Foreign Application Priority Data

| | | |
|---|---|---|
| Feb. 23, 2021 | (CN) | 202110204744.5 |
| May 13, 2021 | (CN) | 202110523923.5 |
| Feb. 10, 2022 | (CN) | 202210125821.2 |

(51) Int. Cl.

| | |
|---|---|
| ***C07D 495/04*** | (2006.01) |
| ***A61K 31/519*** | (2006.01) |
| ***A61P 15/08*** | (2006.01) |

(52) U.S. Cl.

CPC .......... *C07D 495/04* (2013.01); *A61K 31/519* (2013.01); *A61P 15/08* (2018.01)

(58) Field of Classification Search

CPC .................................................. C07D 495/04

See application file for complete search history.

(56) References Cited

U.S. PATENT DOCUMENTS

2019/0055261 A1* 2/2019 Miwa .................. C07D 495/04

FOREIGN PATENT DOCUMENTS

| | | | |
|---|---|---|---|
| EP | 1939204 | A1 | 7/2008 |
| EP | 1939204 | B1 | 1/2013 |
| NZ | 514737 | A | 10/2003 |
| WO | WO 2021023876 | A1 | 2/2021 |

OTHER PUBLICATIONS

Indian Office Action for Application No. 202317063506, mailed May 15, 2015.

International Search Report and Written Opinion for Application No. PCT/CN2022/077112, mailed Apr. 26, 2022.

* cited by examiner

*Primary Examiner* — Rei Tsang Shiao

(74) *Attorney, Agent, or Firm* — Lowenstein Sandler LLP

(57) ABSTRACT

Disclosed in the present invention are a series of fused polycyclic substituted 5-carboxylic acid thienopyrimidine dione compounds and the use thereof. Specifically disclosed are a compound represented by formula (H) and a pharmaceutically acceptable salt thereof.

(II)

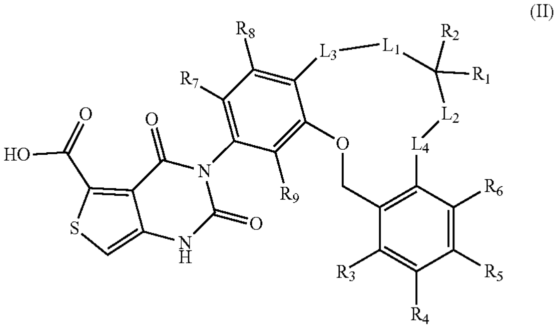

16 Claims, No Drawings

FUSED POLYCYCLIC SUBSTITUTED 5-CARBOXYLIC ACID THIENOPYRIMIDINE DIONE COMPOUND AND USE THEREOF

CROSS REFERENCE TO RELATED APPLICATIONS

This application is a National Stage filing under 35 U.S.C. 371 of International PCT Application No. PCT/CN2022/077112, filed on Feb. 21, 2022, which claims the priority of:

CN202110204744.5, filed on Feb. 23, 2021;
CN202110523923.5, filed on May 13, 2021; and
CN202210125821.2, filed on Feb. 10, 2022. The Chinese Patent Application Nos.
CN202110204744.5, CN202110523923.5 and CN202210125821.2 are incorporated herein by reference as part of the disclosure of the present application.

FIELD OF THE INVENTION

The present disclosure relates to a series of fused polycyclic ring-substituted 5-carboxythienopyrimidinedione compounds and the use thereof, specifically to a compound represented by formula (II) and a pharmaceutically acceptable salt thereof.

BACKGROUND OF THE INVENTION

Endometriosis involves the presence of endometrioid tissue outside the uterus. Endometriosis is not fatal, but results in the symptoms: chronic pelvic pain and dysmenorrhea. Although they are not fatal diseases, they can pose a lot of miseries on the patient's life, including pain, infertility, etc., which are extremely difficult to cure and easy to relapse. In addition, the clinical treatment of this disease has disadvantages such as long medication time, many side effects, and inconvenient administration, etc. According to the World Bank's population calculation in 2017, approximately 190 million women worldwide suffer from endometriosis.

The pathogenesis of endometriosis is not well understood, and current clinical treatment options are either to control estrogen levels, or to control inflammation, or both. For example, the first-line treatment utilizes non-steroidal anti-inflammatory drugs or oral contraceptives, and the second-line treatment includes oral aromatase inhibitors, danazol, or injectable gonadotropin-releasing hormone (GnRH) agonists. However, oral contraceptives have a non-response rate of nearly one-third to one-quarter in patients, while progesterone has a side effect of being prone to obesity, and is especially forbidden for patients who want to become pregnant. Aromatase has side effects such as cardiotoxicity and abnormal lipid metabolism, and gonadotropin-releasing hormone has a side effect of perimenopausal. Polypeptide GnRH receptor agonist or antagonist compounds have many problems, such as obstacles in oral absorption, dosage form, dose volume, drug stability, sustained action, and metabolic stability, etc.

Small molecule compounds can be administered orally, which is convenient and quick, and has obvious advantages. GnRH receptor antagonists directly inhibit the hypothalamus-pituitary-ovarian axis by competitively binding to GnRH receptors and blocking the binding of GnRH to the receptors, thereby inhibiting the secretion of follicle-stimulating hormone and luteinizing hormone, and reducing estrogen levels, which is fast-acting with few side effects. At present, the forefront of the development of small imiecule GnRH receptor antagonists includes Elagolix, which was the first to be marketed. Besides, the FDA approved the second small molecule oral antagonist Relugolix for the first indication for the treatment of advanced prostate cancer in December 2020, while the indication for the treatment of uterine fibroids has been approved in Japan, and the indication for the treatment of endometriosis has entered the third phase of clinical trials. The indications of the third antagonist Linzagolix for the treatment of endometriosis and uterine fibroids are already in the third phase of clinical trials.

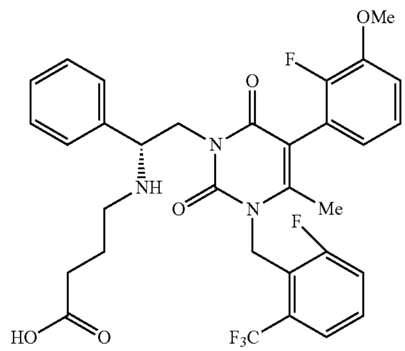

Elagolix

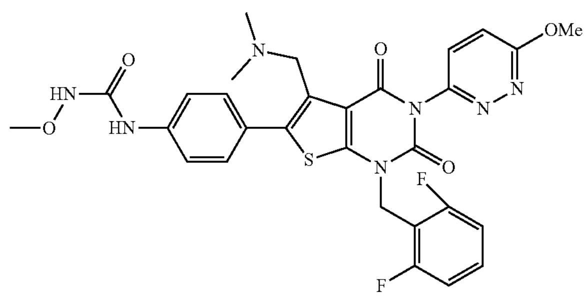

Relugolix

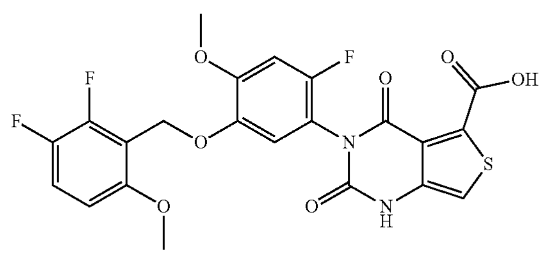

Linzagolix

Although a large number of meaningful clinical trials have been carried out in these areas, there is still a need for continued research to develop more effective small molecule GnRH receptor antagonists.

SUMMARY OF THE INVENTION

The present disclosure provides a novel GnRH receptor antagonist with a fused polycyclic structure, and such structure has significant inhibitory activity on GnRH receptor.

The present disclosure provides a compound represented by formula (II) or a pharmaceutically acceptable salt thereof,

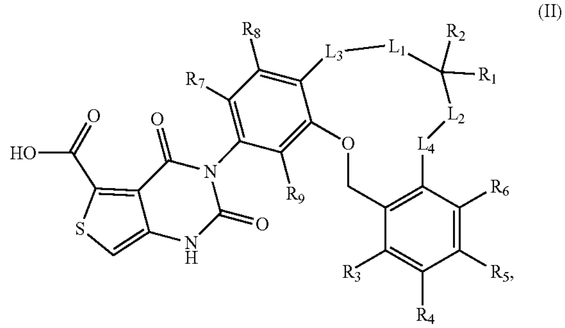

(II)

wherein $L_1$ and $L_2$ are each independently selected from —$(CH_2)_n$—;

$L_3$ and $L_4$ are each independently selected from —$CH_2$—, —CH═CH—; —O— and —S—;

$R_1$ and $R_2$ are each independently selected from H, OH, F, Cl, $C_{1-3}$ alkyl and $C_{1-3}$ alkoxy, wherein the $C_{1-3}$ alkyl and $C_{1-3}$ alkoxy are each independently optionally substituted with 1, 2 or 3 $R_a$;

alternatively, $R_1$ and $R_2$ are taken together with the carbon atom to which they are commonly attached to form a $C_{3-6}$ cycloalkyl or 4- to 6-membered heterocycloakl, wherein the $C_{3-6}$ cycloalkyl or 4- to 6-membered heterocycloalkyl is optionally substituted with 1, 2 or 3 $R_b$;

$R_3$, $R_4$, $R_5$, $R_6$, $R_7$, $R_8$ and $R_9$ are each independently selected from H, F, Cl, Br, I, OH, $NH_2$, CN, $C_{1-3}$ alkyl, $C_{1-3}$ alkoxy and $C_{3-6}$ cycloalkyl, wherein the $C_{1-3}$ alkyl, $C_{1-3}$ alkoxy and $C_{3-6}$ cycloalkyl are each independently optionally substituted with 1, 2 or 3 $R_c$;

n is selected from 0, 1 and 2;

$R_a$, $R_b$ and $R_c$ are each independently selected from H, F, Cl, Br, I, $NH_2$ and OH.

In some embodiments disclosed herein, the above-mentioned $R_1$ and $R_2$ are each independently selected from H, OH, F and $CH_3$, wherein the $CH_3$ is optionally substituted with 1, 2 or 3 F, and other variables are as defined herein.

In some embodiments disclosed herein, the above-mentioned $R_1$ and $R_2$ are each independently selected from H, and other variables are as defined herein.

In some embodiments disclosed herein, the above-mentioned $R_1$ and $R_2$ are taken together with the atom to which they are commonly attached to form a cyclopropyl, cyclobutyl, cyclopentyl, oxetanyl or azetidinyl, wherein the cyclopropyl, cyclobutyl, cyclopentyl, oxetanyl or azetidinyl is optionally substituted with 1, 2 or 3 $R_b$, and other variables are as defined herein.

In some embodiments disclosed herein, the above-mentioned $R_1$ and $R_2$ are taken together with the atom to which they are commonly attached to form a cyclopropyl, cyclobutyl, cyclopentyl, oxetanyl and azetidinyl, wherein the cyclopropyl, cyclobutyl, cyclopentyl, oxetanyl and azetidinyl is optionally substituted with 1, 2 or 3 F, and other variables are as defined herein.

In some embodiments disclosed herein, the above-mentioned $R_1$ and $R_2$ are taken together with the atom to which they are commonly attached to form a

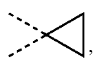, and other variables are as defined herein.

In some embodiments disclosed herein, the above-mentioned $R_3$, $R_4$, $R_5$ and $R_6$ are each independently selected from H, F, Cl, OH, $NH_2$, CN, $CH_3$, $CF_3$, $OCH_3$ and $OCF_3$, and other variables are as defined herein.

In some embodiments disclosed herein, the above-mentioned $R_3$, $R_4$, $R_5$ and $R_6$ are each independently selected from H and F, and other variables are as defined herein.

In some embodiments disclosed herein, the above-mentioned structural moiety

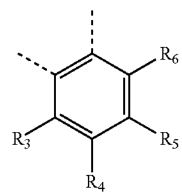

is selected from

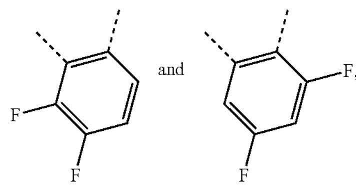

and other variables are as defined herein.

In some embodiments disclosed herein, the above-mentioned $R_7$, $R_8$ and $R_9$ are each independently selected from H, F, Cl, OH, $NH_2$, CN, $CH_3$, $CF_3$, $OCH_3$ and $OCF_3$, and other variables are as defined herein.

In some embodiments disclosed herein, the above-mentioned $R_7$, $R_8$ and $R_9$ are each independently selected from H and F, and other variables are as defined herein.

In some embodiments disclosed herein, the above-mentioned structural moiety

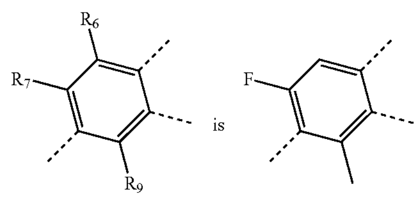

and other variables are as defined herein.

In some embodiments disclosed herein, the above-mentioned structural moiety

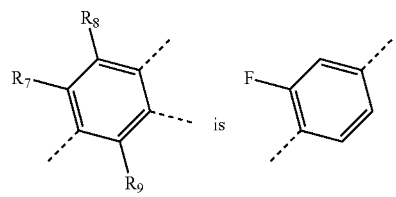

and other variables are as defined herein.

In some embodiments disclosed herein, the above-mentioned $L_3$ and $L_4$ are each independently selected from O, and other variables are as defined herein.

In some embodiments disclosed herein, the above-mentioned n is selected from 1 and 2, and other variables are as defined herein.

In some embodiments disclosed herein, the above-mentioned structural moiety

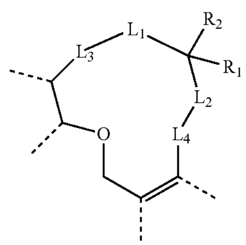

is selected from

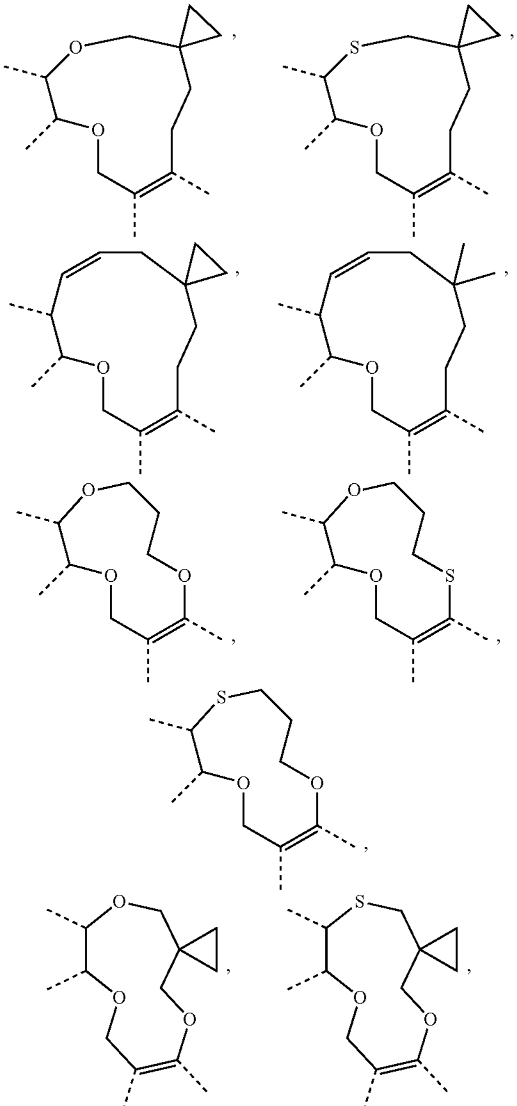

-continued

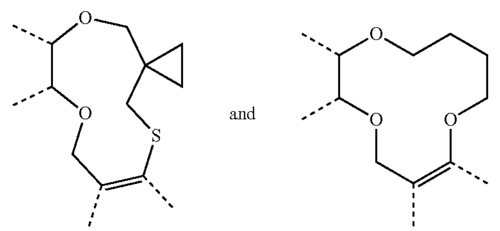

and other variables are as defined herein.

In some embodiments disclosed herein, the above-mentioned structural moiety

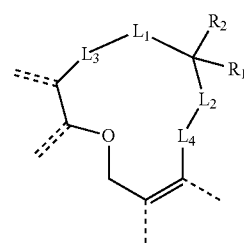

is selected from

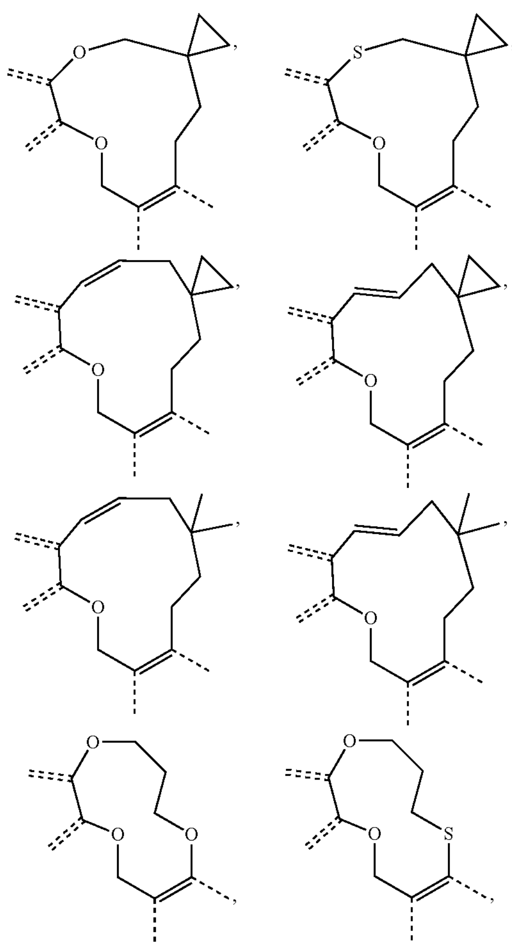

-continued

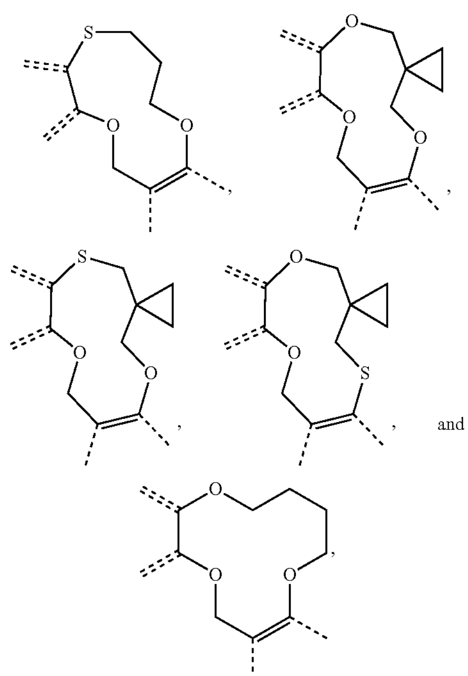

and and other variables are as defined herein.

In some embodiments disclosed herein, the above-mentioned structural moiety

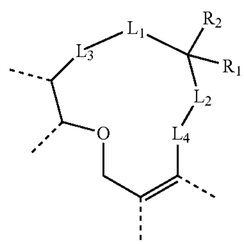

is selected from

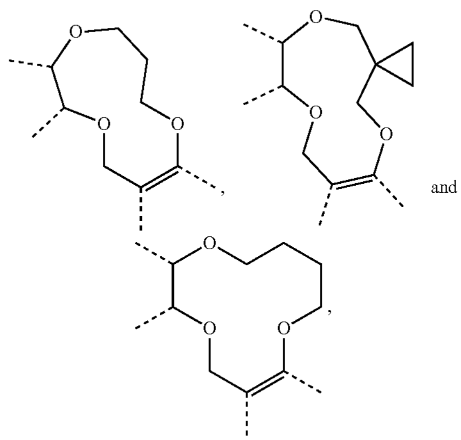

and and other variables are as defined herein.

In some embodiments disclosed herein, the above-mentioned structural moiety

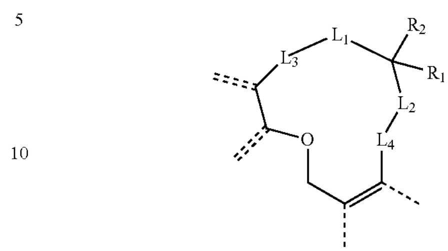

is selected from

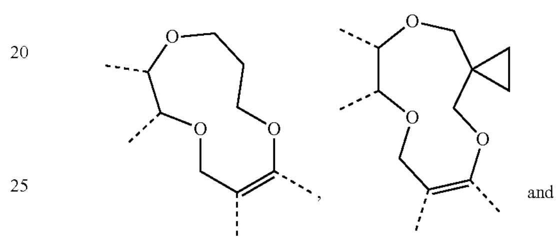

and

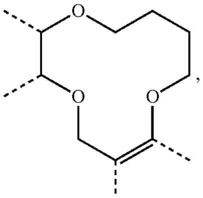

and other variables are as defined herein.

In some embodiments disclosed herein, disclosed is the above-mentioned compound, or a pharmaceutically acceptable salt thereof, wherein the compound is (I-1)

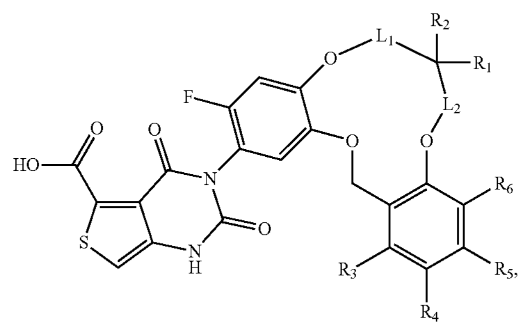

wherein $L_1$, $L_2$, $R_1$, $R_2$, $R_3$, $R_4$, $R_5$ and $R_6$ are as defined herein, respectively.

The present disclosure also provides a compound as shown in formula (I) or a pharmaceutically acceptable salt thereof, (I)

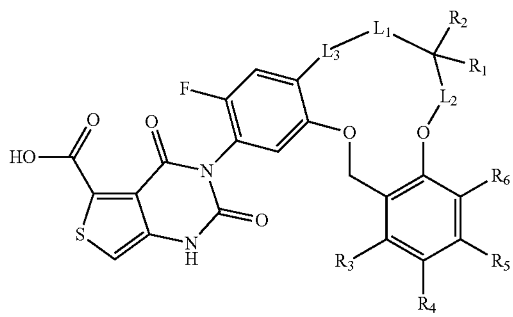

wherein $L_1$ and $L_2$ are each independently selected from $—(CH_2)_n—$;

$L_3$ and $L_4$ are each independently selected from $—CH_2—$, $—CH═CH—$, —O— and —S—;

$R_1$ and $R_2$ are each independently selected from H, OH, F, Cl, $C_{1-3}$ alkyl and $C_{1-3}$ alkoxy, wherein the $C_{1-3}$ alkyl and $C_{1-3}$ alkoxy is optionally substituted with 1, 2 or 3 $R_a$;

alternatively, $R_1$ and $R_2$ are taken together with the atom to which they are commonly attached to form a $C_{3-6}$ cycloalkyl or 4- to 6-membered heterocycloalkyl, wherein the $C_{3-6}$ cycloalkyl or 4- to 6-membered heterocycloalkyl is optionally substituted with 1, 2 or 3 $R_b$;

$R_3$, $R_4$, $R_5$ and $R_6$ are each independently selected from H, F, Cl, Br and I;

n is selected from 0, 1 and 2;

$R_a$ and $R_b$ are each independently selected from H, F, Cl, Br, and I;

The "4- to 6-membered heterocycloalkyl" comprises 1, 2 or 3 heteroatoms selected from N, NH, O and S.

The present disclosure also includes some embodiments obtained by any combination of the above variables.

The present disclosure also provides the composIs as shown below, or pharmaceutically acceptable salts thereof,

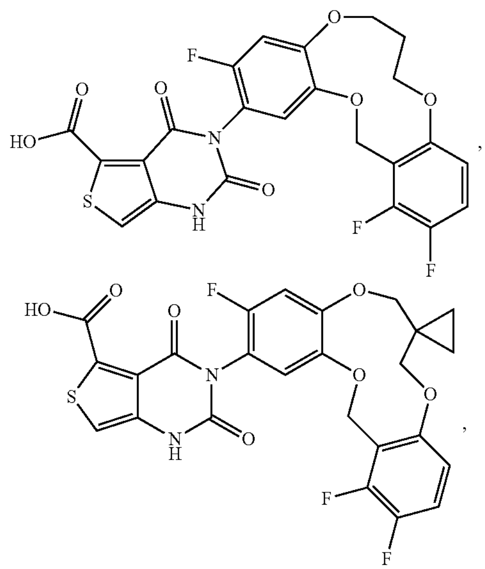

, ,

-continued

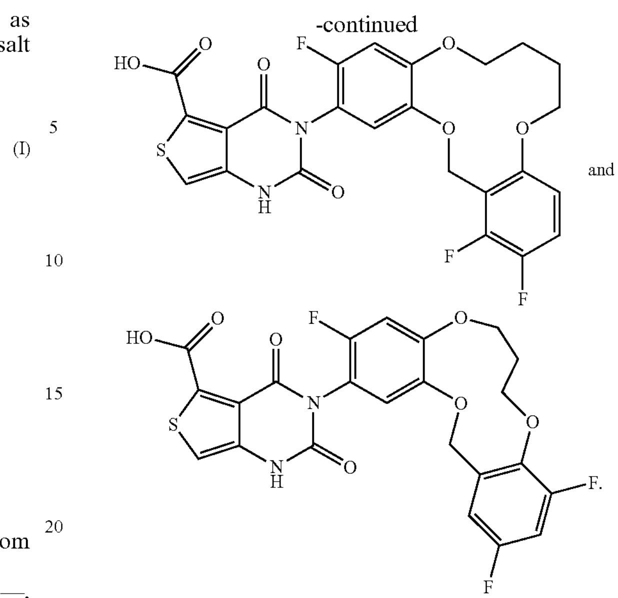

and

The present disclosure also provides the use of the above compounds or pharmaceutically acceptable salts thereof in the manufacture of a medicatnent related to a GnRH receptor antagonist.

In some embodiments of the present disclosure, the above-mentioned medicament related to a GnRH receptor antagonist is a medicament for preventing andlor treating diseases related to endometriosis and/or uterine fibroids.

Technical Effect

The compound of the present disclosure has a significant inhibitory effect on the human gonadotropin-releasing hormone receptor, and can significantly inhibit the increase of the volume of endometriotic lesions in mice with excellent efficacy; PK results show that the compounds of the present disclosure have high exposure in plasma, low clearance, long half-life, and high oral bioavailability, exhibit excellent pharmacokinetic properties, and are good molecules for the development of oral administration.

Definition and Term

Unless otherwise specified, the following terms and phrases used herein are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" means a salt of compounds disclosed herein that is prepared by reacting the compound having a specific substituent disclosed herein with a relatively non-toxic acid or base. When compounds disclosed herein contain a relatively acidic functional group, a base addition salt can be obtained by bringing the compound into contact with a sufficient amount of base in a pure solution or a suitable inert solvent. The pharmaceutically acceptable base addition salt includes a salt of sodium, potassium, calcium, ammonium, organic amine or magnesium or similar salts. When compounds disclosed herein contain a relatively basic functional group, an acid addition salt can be obtained by bringing the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds disclosed herein contain both basic and acidic functional groups and can be converted to any base or acid addition salt.

The pharmaceutically acceptable salt disclosed herein can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof.

Compounds disclosed herein may be present in a specific geometric or stereoisomeric form. The present disclosure contemplates all such compounds, including cis and trans isomers, (−)- and (+)-enantiomers, (R)- and (S)-enantiomers, diastereoisomer, (D)-isomer, (L)-isomer, and a racemic mixture and other mixtures, for example, a mixture enriched in enantiomer or diastereoisomer, all of which are encompassed within the scope disclosed herein. The substituent such as alkyl may have an additional asymmetric carbon atom. All these isomers and mixtures thereof are encompassed within the scope disclosed herein.

Unless otherwise specified, the term "enantiomer" or "optical isomer" refers to stereoisomers that are in a mirrored relationship with each other.

Unless otherwise specified, the term "cis-trans isomer" or "geometric isomer" is produced by the inability of a double bond or a single bond between ring-forming carbon atoms to rotate freely.

Unless otherwise specified, the term "diastereomer" refers to a stereoisomer in which two or more chiral centers are contained in a molecule and is in a non-mirrored relationship between molecules.

Unless otherwise specified, "(+)" means dextroisomer, "(−)" means levoisomer, and "(±)" means racemate.

Unless otherwise specified, a wedged solid bond ( ) and a wedged dashed bond ( ) indicate the absolute configuration of a stereocenter; a straight solid bond ( ) and a straight dashed bond ( ) indicate the relative configuration of a stereocenter; a wavy line ( )indicates a wedged solid bond ( ) or a wedged dashed bond ( ); or a wavy line ( ) indicates a straight solid bond ( ) and a straight dashed bond ( ).

Unless otherwise specified, when a double bond structure such as a carbon-carbon double bond, a carbon-nitrogen double bond, and a nitrogen-nitrogen double bond is present in a compound, and each atom on the double bond is attached to two different substituents (in the double bond containing a nitrogen atom, a pair of lone pair electrons on the nitrogen atom is considered as one of the substituents to which it is attached), the compound represents (Z) isomer, (E) isomer, or a mixture of two isomers of the compound, if the atoms on the double bond in the compound are attached to their substituents by a wavy line ( ). For example, the compound having following formula (A) means that the compound is present as a single isomer of formula (A-1) or formula (A-2) or as a mixture of two isomers of formula (A-1) and formula (A-2) and the compound having following formula (B) means that the compound is present as a single isomer of formula (B-1) or formula (B-2) or as a mixture of two isomers of formula (B-1) and formula (B-2), The compound having following formula (C) means that the compound is present as a single isomer of formula (C-1) or formula (C-2) or as a mixture of two isomers of formula (C-1) and formula (C-2).

(A)

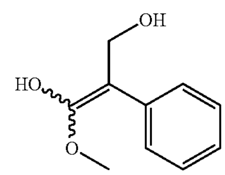

(A-1)

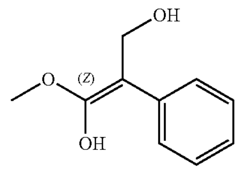

(A-2)

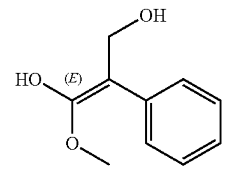

(B)

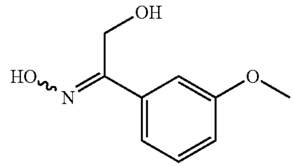

(B-1)

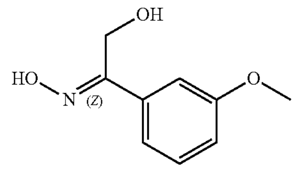

(B-2)

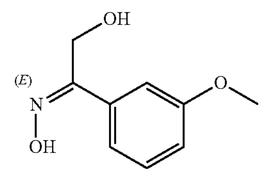

-continued (C)

(C-1)

(C-2)

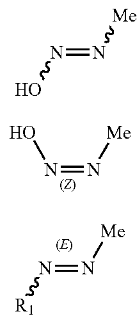

Unless otherwise specified, the terms "tautomer" or "ta: citomeric form" means that different functional groups are in dynamic equilibrium at room temperature and can he rapidly converted into each other. If tautomers are possible (as in solution), a chemical equilibrium of tautomers can be achieved. For example, proton tautomers (also known as prototropic tautomers) include interconversions by proton transfer, such as keto-enol isomerization and imine-enamine isomerization. Valence tautomers include interconversions by recombination of some bonding electrons. A specific example of keto-enol tautomerization is interconversion between two tautomers pentane-2,4-dione and 4-hydroxy-pent-3-en-2-one.

Unless otherwise specified, the term "enriched in one isomer", "isomer enriched", "enriched in one enantiomer" or "enantiomeric enriched" means that the content of one isomer or enantiomer is less than 100%, and the content of the isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless otherwise specified, the term "isomer excess" or "enantiomeric excess" means the difference between the relative percentages of two isomers or two enantiomers. For example, if one isomer or enantiomer is present in an amount of 90% and the other isomer or enantiomer is present in an amount of 10%, the isomer or enantiomeric excess (ee value) is 80%.

Compounds disclosed herein may contain an unnatural proportion of atomic isotopes at one or more of the atoms that make up the compounds. For example, a compound may be labeled with a radioisotope such as tritium ($^3$H), iodine-125 ($^{125}$I) or C-14($^{14}$C). For another example, hydrogen can be replaced by heavy hydrogen to form a deuterated drug. The bond between deuterium and carbon is stronger than that between ordinary hydrogen and carbon. Compared with undeuterated drugs, deuterated drugs have advantages of reduced toxic side effects, increased drug stability, enhanced efficacy, and prolonged biological half-life of drugs. All changes in the isotopic composition of compounds disclosed herein, regardless of radioactivity, are included within the scope of the present disclosure.

The term "optional" or "optionally" means that the subsequent event or condition may occur but not requisite, that the term includes the instance in which the event or condition occurs and the instance in which the event or condition does not occur.

The term "substituted" means one or more than one hydrogen atoms) on a specific atom are substituted by a substituent, including deuterium and hydrogen variants, as long as the valence of the specific atom is normal and the substituted compound is stable. When the substituent is oxo (i.e, =O), it means two hydrogen atoms are substituted. Positions on an aromatic ring cannot be substituted by oxo. The term "optionally substituted" means an atom can be substituted by a substituent or not, unless otherwise specified, the species and number of the substituent may be arbitrary so long as being chemically achievable.

When any variable (such as R) occurs in the constitution or structure of the compound more than once, the definition of the variable at each occurrence is independent. Thus, for example, if a group is substituted by 0 to 2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as $-(CRR)_0-$, it means that the linking group is a single bond.

When one of variables is a single bond, it means that the two groups linked by the single bond are connected directly. For example, when L in A-L-Z represents a single bond, the structure of A-L-Z is actually A-Z.

Unless otherwise specified, when a group has one or more connectable sites, any one or more sites of the group can be connected to other groups through chemical bonds. Where the connection position of the chemical bond is variable, and there is H atom(s) at a connectable site(s), when the connectable site(s) having H atoms) is connected to the chemical bond, the number of H atom(s) at this site will correspondingly decrease as the number of the connected chemical bond increases, and the group will become a group of corresponding valence. The chemical bond between the site and other groups can be represented by a straight solid bond (), a straight dashed bond (), or a wavy line (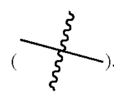).

For example, the straight solid bond in $-OCH_3$ indicates that the group is connected to other groups through the oxygen atom in the group; the straight dashed bond in

indicates that the group is connected to other groups through two ends of the nitrogen atom in the group; the wavy line in

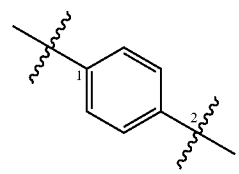 [SMILES: *c1ccc(*)cc1]

indicates that the group is connected to other groups through the 1- and 2-carbon atoms in the phenyl group;

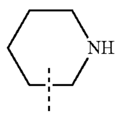

indicates that any connectable site on the piperidinyl group can be connected to other groups through one chemical bond, including at least four connection ways,

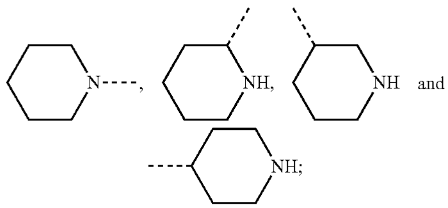

even if a H atom is drawn on —N—,

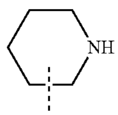

still includes the connection way of

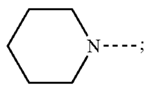

it's just that when one chemical bond is connected, the H at this site will be reduced by one, and the group will become the corresponding monovalent piperidinyl group;

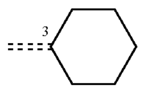

indicates that the carbon atom at the 3-position in this cyclohexyl group is connected to another group through a double bond.

Unless otherwise specified, the term "$C_{1-3}$ alkyl" alone or in combination with other terms respectively represents a linear or branched saturated hydrocarbon group composed of 1 to 3 carbon atoms. The $C_{1-3}$ alkyl includes $C_{1-2}$ alkyl, $C_{2-3}$ alkyl, etc. It may be monovalent (such as methyl), divalent (such as methylene) or multivalent (such as methenyl). Examples of the $C_{1-3}$ alkyl include, but are not limited to, methyl (Me), ethyl (Et), propyl (including n-propyl and isopropyl), and the like.

Unless otherwise specified, the term "$C_{1-3}$ alkoxy" alone or in combination with other terms respectively represents alkyl groups containing 1 to 3 carbon atoms and attached to the remainder of a molecule by an oxygen atom. The $C_{1-3}$ alkoxy group includes $C_{1-2}$, $C_{2-3}$, $C_3$, and $C_2$ alkoxy groups, and the like. Examples of $C_{1-3}$ alkoxy groups include, but are not limited to, methoxy, ethoxy, propoxy (including n-propoxy and isopropoxy), and the like.

Unless otherwise specified, "$C_{3-6}$ cycloalkyl" represents a saturated monocyclic hydrocarbon group composed of 3 to 6 carbon atoms. The $C_{3-6}$ cycloalkyl includes $C_{3-5}$, $C_{4-5}$ and $C_5$-6 cycloalkyl, etc.; it may be monovalent, divalent or multivalent. Examples of the $C_{3-6}$ cycloalkyl include, but are not limited to, cyclopropyl, cyclobutyl, cyclopentyl, cyclohexyl, etc.

Unless otherwise specified, the term "4- to 6-membered heterocycloalkyl" alone or in combination with other terms respectively represents a saturated monocyclic group composed of 4 to 6 ring atoms, in which 1, 2, 3 or 4 ring atoms are heteroatoms independently selected from O, S and N, and the remainder is carbon atom, wherein the nitrogen atom is optionally quaternized, and the nitrogen and sulfur heteroatoms are optionally oxidized (i.e., NO and $S(O)_p$, wherein p is 1 or 2). In addition, with respect to the "4- to 6-membered heterocycloalkyl", the heteroatom may be present on the position of attachment of the heterocycloalkyl group to the remainder of a molecule. The 4- to 6-membered heterocycloalkyl includes 5-6 membered, 4 membered, 5 membered, and 6 membered heterocycloalkyl, etc. Examples of the 4- to 6-membered heterocycloalkyl include, but are not limited to, azetidinyl, oxetanyl, thietanyl, pyrrolidinyl, pyrazolidinyl, imidazolidinyl, tetrahydrothienyl (including tetrahydrothien-2-yl and tetrahydrothien-3-yl and the like), tetrahydrofuranyl (including tetrahydrofuran-2-yl and the like), tetrahydropyranyl, piperidinyl (including 1-piperidinyl, 2-piperidinyl and 3-piperidinyl and the like), piperazinyl (including 1-piperazinyl and 2-piperazinyl and the like), morpholinyl (including 3-morpholinyl and 4-morpholinyl and the like), dioxanyl, dithianyl, isoxazolidinyl, isothiazolidinyl, 1,2-oxazinyl, 1,2-thiazinyl, and hexahydropyridazinyl, and the like.

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$, also includes any range from n to n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$ and $C_{9-12}$, etc.; similarly, n membered to n+m membered indicates that the number of atoms on a ring is n to n+m, for example, 3-12 membered ring includes 3 membered ring, 4 membered ring, 5 membered ring, 6 membered ring, 7 membered ring, 8 membered ring, 9 membered ring, 10 membered ring, 11 membered ring, and 12 membered ring, also includes any range from n to n+m, for example, 3-12 membered ring includes 3-6 merrihered ring, 3-9 membered ring, 5-6 membered ring, 5-7 membered ring, 6-7 membered ring, 6-8 membered ring, and 6-10 membered ring, and the like.

Compounds disclosed herein can be prepared by a variety of synthetic methods well known to those skilled in the art, including the following enumerated embodiment, the embodiment formed by the following enumerated embodiment in combination with other chemical synthesis methods, and equivalent replacement well known to those skilled in the art. Alternative embodiments include, but are not limited to the embodiment disclosed herein.

The structures of compounds disclosed herein can be confirmed by conventional methods well known to those skilled in the art. If the present disclosure relates to an absolute configuration of a compound, the absolute configuration can be confirmed by conventional techniques in the art, such as single crystal X-Ray diffraction (SXRD). In the single crystal X-Ray diffraction (SXRD), the diffraction intensity data of the cultivated single crystal is collected using a Balker D8 venture diffractometer with a light source of CuKα radiation in a scanning mode of φ/ω scan; after collecting, the relevant data, the crystal structure is further analyzed by the direct method (Shelxs97) to confirm the absolute configuration.

The following abbreviations are used in this disclosure: DMSO represents dimethyl sulfoxide; MeOH represents methanol; ACN represents acetonitrile; DEA represents diethylamine; $CO_2$ represents carbon dioxide; psi represents pounds per square inch; Ac represents acetyl, Ph represents phenyl, DMAC represents N,N-dimethylacetamide, Solutol represents polyethylene glycol-15 hydroxystearate; and PEG represents polyethylene glycol.

Solvents used in the present disclosure are commercially available. Compounds are named according to general naming principles in the art or by ChemDraw® software, and commercially available compounds are named with their vendor directory names.

DETAILED DESCRIPTION OF THE INVENTION

The present disclosure is described in detail below by means of examples. However, it is not intended that these examples have any disadvantageous hmitations to the present disclosure. The present disclosure has been described in detail herein, and embodiments are also disclosed herein. It will be apparent to those skilled in the art that various changes and modifications may be made to the embodiments disclosed herein without departing from the spirit and scope disclosed herein.

Reference Example 1: Intermediate BB-1

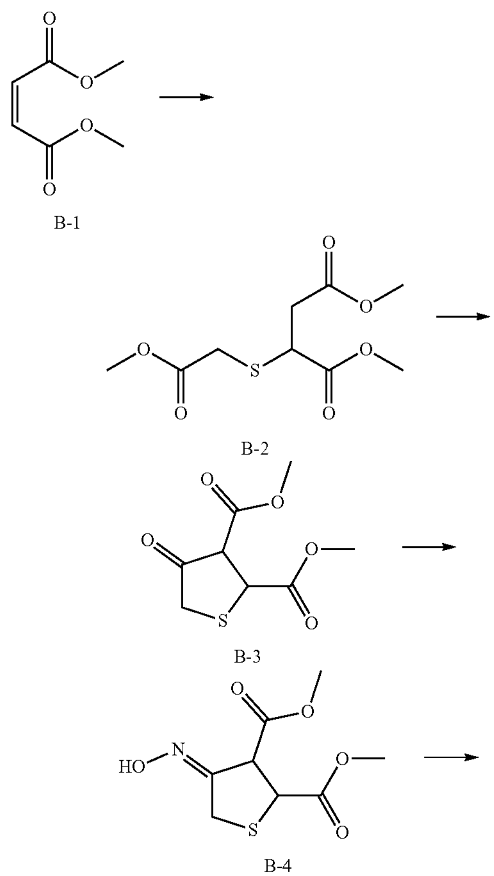

B-1

B-2

B-3

B-4

-continued

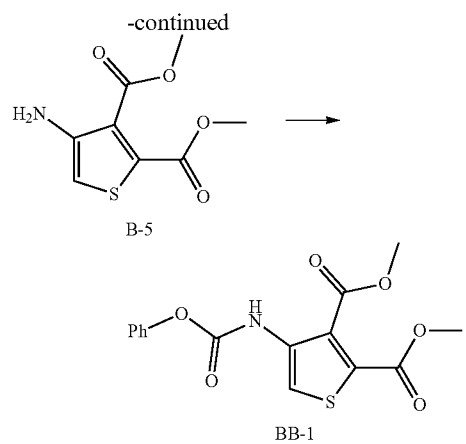

B-5

BB-1

Step 1

To a solution of compound B-1 (dimethyl maleate, 50 g, 346.92 mmol) and methyl thioglycolate (37.01 g, 348.68 mmol) in tetrahydrofuran (300 mL) was added piperidine (886.18 mg, 10.41 mmol.), and the mixture was stirred at 25° C. for 2 hours. After completion of reaction as judged by thin layer chromatography plate (petroleum ether:ethyl acetate=5:1), 300 ml of water was added. The mixture was extracted twice with ethyl acetate, 200 ml each time. The combined organic phase was washed with 200 ml of saturated brine, dried over anhydrous sodium sulfate, and filtered. The filtrate was concentrated to dryness under reduced pressure to give compound B-2.

$^1$H NMR (400 MHz, $CDCl_3$) δ=3.89-3.81 (m, 1H), 3.76 (s, 3H), 3.75 (d, 3H), 3.69 (s, 3H), 3.55-3.32 (m, 2H), 3.00 (m, 1H), 2.73 (m, 1H).

Step 2

Sodium (278 g, 120.92 mmol) was added to methanol (10 mL) below 20° C. The mixture was stirred below 64° C. until the solid was dissolved, so that the mixture was configured as a solution of sodium methanol in methanol. The solution was cooled to 20° C., and then added to a solution of B-2 (10 g, 39.96 mmol) tetrahydrofuran (20 mL). The reaction solution was stirred at 66° C. under nitrogen for 3 h. Isopropyl ether (100 mL) and acetic acid (1 mL) were added. The mixture was cooled to 20° C., and then filtered. The filter cake was added to a mixture of phosphoric acid (10 mL) and water (20 mL), and the mixture was extracted twice with ethyl acetate, 20 mL each time. The combined organic phase was washed with 30 mL of saturated brine, dried over anhydrous sodium sulfate, and filtered. The filtrate was concentrated to dryness under reduced pressure to give compound B-3.

Step 3

A mixture of compound B-3 (7.4 g, 33.91 mmol), pyridine (4.03 g, 50.89 mmol), and hydroxylamine hydrochloride (2.47 g, 35.57 mmol) was stirred at 50° C. for 2 h. To the reaction solution were added 2 ml, of phosphoric acid and 20 mL of water, and the mixture was extracted twice with ethyl acetate, 20 mL each time. The organic layers were combined, washed with 20 mL of saturated sodium bicarbonate and once with 20 mL of saturated aqueous sodium chloride, dried over anhydrous sodium sulfate, and filtered. The filtrate was concentrated to dryness under reduced pressure to give compound B-4.

Step 4

To compound B-4 (5.2 g, 22.29 mmol) in acetic acid (5 mL) vas added 4 moles per liter of hydrochloric acid/ethyl acetate (52.00 mL), and the reaction solution was stirred at 25° C. for 12 hours. The reaction solution was filtered and the filter cake was concentrated to dryness under reduced pressure to give the compound B-5 hydrochloride.

MS-CSI calculated for $[M+H-MeOH]^+$ 184.0, found: 184.1.

Step 5

To compound B-5 (2 g, 7.95 mmol, hydrochloride) in tetrahydrofuran (20 mL) and water (10 mL) was added potassium carbonate (1.65 g, 11.92 mmol). Phenyl chloroformate (2.49 g, 15.89 mmol) was added dropwise at 5-10° C. The reaction solution was stirred at 5-10° C. for 1 h. To the reaction solution was added 50 ml of water, and the mixture was extracted twice with ethyl acetate, 50 ml each time. The organic phases were combined, washed with 50 ml of saturated brine, dried over anhydrous sodium sulfate, and filtered. The filtrate was concentrated to dryness, and ethyl acetate (5 ml) and petroleum ether (50 ml) were added. The mixture was slurried at 30° C. for 30 min, and filtered. The filter cake was dried under reduced pressure to give compound BB-1.

MS-EST calculated for $[M+H]^+$ 336.1, found: 336.1.

Reference Example 2: Intermediate BB-2

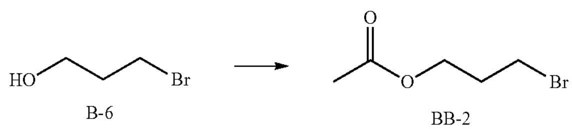

B-6

BB-2

Step 1

To a solution of compound B-6 (3-bromopropanol, 5 g, 35.97 mmol) and 4-dimethylaminopyridine (439.49 mg, 3.6 mmol) in dichloromethane (25 mL) was added dropwise a solution of acetic anhydride (4.04 g, 39.57 mmol) in dichloromethane (5 mL). The mixture was warmed to 25° C. and stirred at 25° C. for 4 h. The reaction solution was washed with 1 mol/L hydrochloric acid (10 mL×2). The aqueous phase was collected and extracted with dichloromethane (30 mL×3). The combined organic phase was washed with saturated aqueous sodium bicarbonate (10 mL×2) and with saturated brine (10 mL×2). The organic phase was collected, dried over anhydrous sodium sulfate, and filtered. The filtrate was concentrated to give intermediate compound BB-2.

$^1H$ NMR (400 MHz, $CDCl_3$) δ=4.18-4.25 (m, 2 H), 3.44-3.51 (m, 2 H), 2.15-2.23 (m, 2 H), 2.07 (s, 3 H).

Example 1

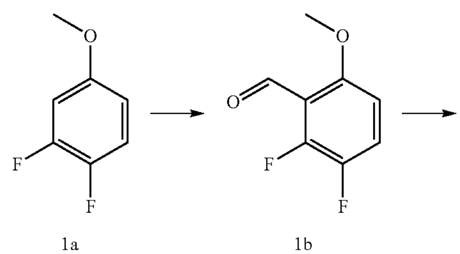

1a

1b

-continued

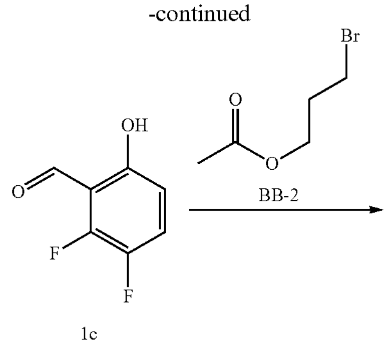

1c

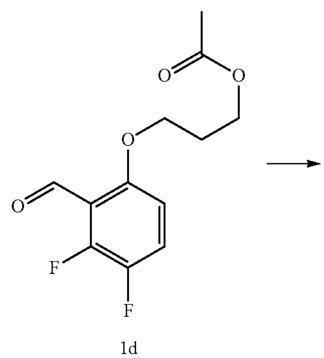

1d

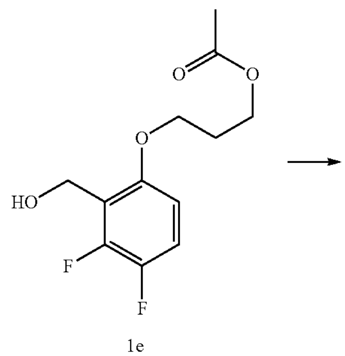

1e

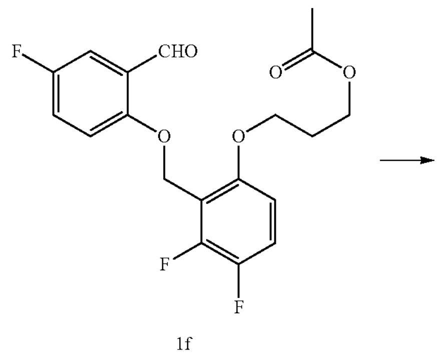

1f

-continued

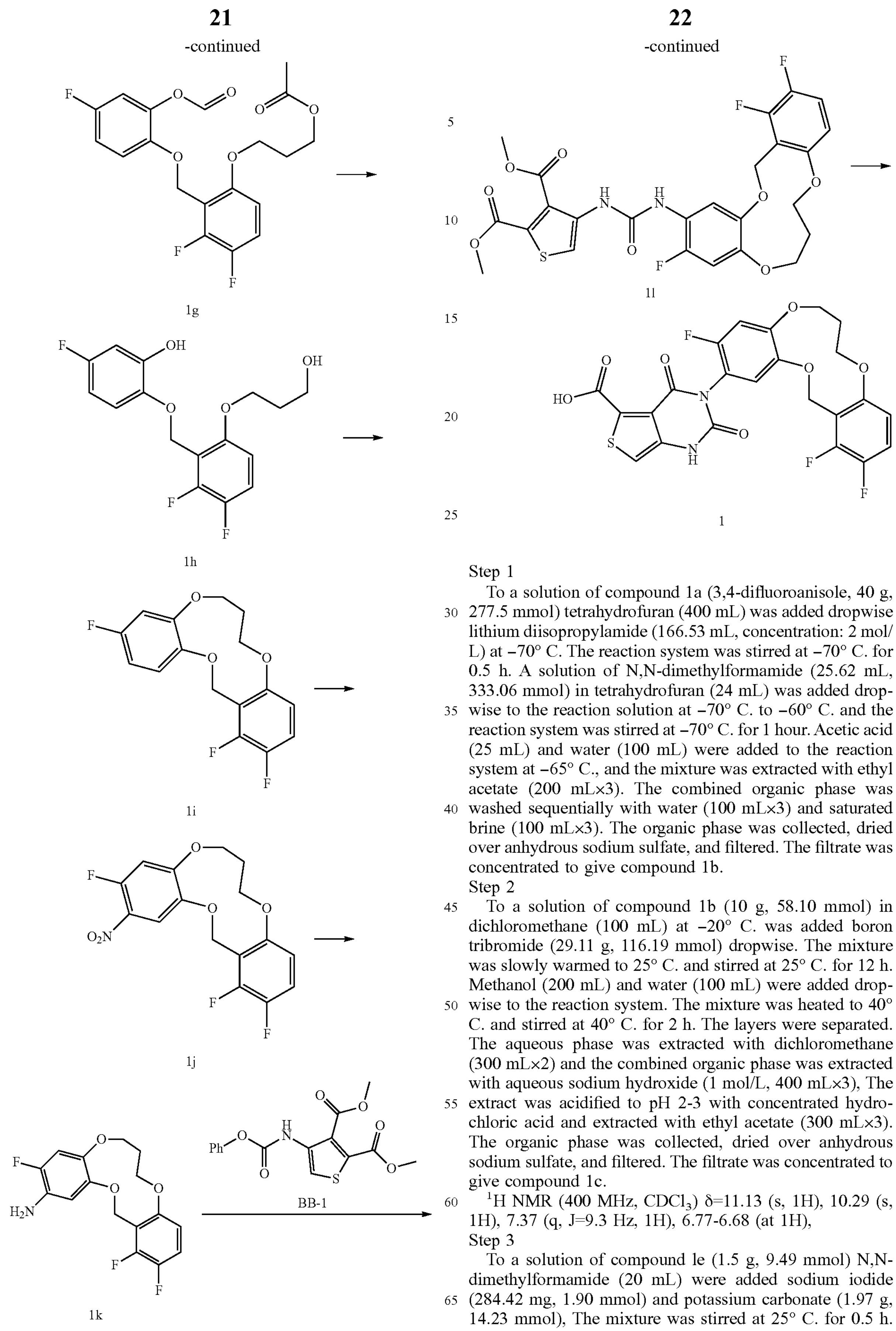

1g

1h

1i

1j

1k

BB-1

-continued

1l

1

Step 1

To a solution of compound 1a (3,4-difluoroanisole, 40 g, 277.5 mmol) tetrahydrofuran (400 mL) was added dropwise lithium diisopropylamide (166.53 mL, concentration: 2 mol/L) at −70° C. The reaction system was stirred at −70° C. for 0.5 h. A solution of N,N-dimethylformamide (25.62 mL, 333.06 mmol) in tetrahydrofuran (24 mL) was added dropwise to the reaction solution at −70° C. to −60° C. and the reaction system was stirred at −70° C. for 1 hour. Acetic acid (25 mL) and water (100 mL) were added to the reaction system at −65° C., and the mixture was extracted with ethyl acetate (200 mL×3). The combined organic phase was washed sequentially with water (100 mL×3) and saturated brine (100 mL×3). The organic phase was collected, dried over anhydrous sodium sulfate, and filtered. The filtrate was concentrated to give compound 1b.

Step 2

To a solution of compound 1b (10 g, 58.10 mmol) in dichloromethane (100 mL) at −20° C. was added boron tribromide (29.11 g, 116.19 mmol) dropwise. The mixture was slowly warmed to 25° C. and stirred at 25° C. for 12 h. Methanol (200 mL) and water (100 mL) were added dropwise to the reaction system. The mixture was heated to 40° C. and stirred at 40° C. for 2 h. The layers were separated. The aqueous phase was extracted with dichloromethane (300 mL×2) and the combined organic phase was extracted with aqueous sodium hydroxide (1 mol/L, 400 mL×3), The extract was acidified to pH 2-3 with concentrated hydrochloric acid and extracted with ethyl acetate (300 mL×3). The organic phase was collected, dried over anhydrous sodium sulfate, and filtered. The filtrate was concentrated to give compound 1c.

$^{1}$H NMR (400 MHz, $CDCl_3$) δ=11.13 (s, 1H), 10.29 (s, 1H), 7.37 (q, J=9.3 Hz, 1H), 6.77-6.68 (at 1H),

Step 3

To a solution of compound le (1.5 g, 9.49 mmol) N,N-dimethylformamide (20 mL) were added sodium iodide (284.42 mg, 1.90 mmol) and potassium carbonate (1.97 g, 14.23 mmol), The mixture was stirred at 25° C. for 0.5 h. Then compound BB-2 (2.06 g, 11.39 mmol) was added and the mixture was heated to 60° C. and stirred at 60° C. for 12 hours. The reaction system was poured into 30 mL of water and the mixture was extracted with ethyl acetate (50 mL×5). The combined organic phase was washed with water (20 mL×5) and once with saturated brine. The organic phase was dried over anhydrous sodium sulfate, and filtered. The filtrate was concentrated to give compound rtd.

$^1$H NMR (400 MHz, $CDCl_3$) δ=10.45-10.38 (m, 1H), 7.37-7.28 (m, 1H), 6.74-6.65 (m, 1H), 4.28 (t, J=6.2 Hz, 2H), 4.16-4.13 (m, 2H), 2.22-2.16 (m, 2H), 2.06 (s, 3H).

Step 4

To a solution of compound 1d (3.25 g, 12.59 mmol) in tetrahydrofuran (30 mL) at 0° C. was added a solution of sodium horohydride (490 mg, 12.95 mmol) in water (3 mL), and the reaction system was stirred at 0° C. for 0.5 h. Water (10 mL) was added to the reaction system at 0° C., and the mixture was extracted with ethyl acetate (30 mL×3). The combined organic phase was washed with water (10 mL×2) and with saturated brine (10 mL×), The organic phase was dried over anhydrous sodium sulfate, and filtered. The filtrate was concentrated to give compound 1e.

Step 5

To a solution of compound 1e (2.65 g, 10.18 mmol) and 5-fluoro-2-hydroxybenzaldehyde (1.57 g, 11.2 mmol) in tetrahydrofuran (20 mL) was added tri-n-butylphosphine (3.71 g, 18.33 mmol), and the mixture was stirred for 0.1 h. Then a solution of azodicarbonyldipiperidine (4.62 g, 18.33 mmol) in tetrahydrofuran (5 mL) was added dropwise at 0° C. The mixture was warmed to 25° C. and stirred at 25° C. for 12 h. The reaction system was poured into 10 mL of water, and the mixture was extracted with ethyl acetate (30 mL×3). The combined organic phase was washed with water (10 mL×3) and with brine (10 mL×3). The collected organic phase was dried over anhydrous sodium sulfate, and filtered. The filtrate was concentrated. The crude product was purified by column chromatography (silica gel, petroleum ether: ethyl acetate=1/0~20/1) to give compound 1f.

$^1$H NMR (400 MHz, $CDCl_3$) δ=10.31 (d,=3.2 Hz, 1H), 7.49 (dd, J=3.2, 8.4 Hz, 1H), 7.33-7.27 (m, 1H), 7.23-7.18 (m, 1H), 7.18-7.11 (m, 1H), 6.72-6.57 (m, 1H), 5.25 (d, J=2.8 Hz, 2H), 4.19 (t, J=6.2 Hz, 2H), 4.06 (t, J=6.2 Hz, 2H), 2.09-2.06 (m, 2H), 2.04 (s, 3H).

Step 6

To a solution of compound 1f (1.04 g, 2.72 mmol) in dichloromethane (10 mL) at 0° C. was added m-chloroperoxybenzoic acid (1.66 g, 85% purity, 8.16 mmol), and the mixture was warmed to 25° C. and stirred at 25° C. for 12 h. To the reaction solution was added 2 mL of saturated aqueous sodium sulfite solution, and then 10 mL of water was added. The mixture was extracted with ethyl acetate (30 mL×3). The combined organic phase was washed with water (10 mL×2) and with saturated brine (10 mL×2), dried over anhydrous sodium sulfate, and filtered. The filtrate was concentrated to give a crude product. The crude product was purified by preparative chromatography (petroleum ether: ethyl acetate=3:1) to give compound 1g.

$^1$H NMR (400 MHz, $CDCl_3$) δ=8.19 (s, 1H), 7.18-7.08 (m, 2H), 7.00-6.93 (m, 1H), 6.89 (dd, J=3.2, 8.4 Hz, 1H), 6.63-6.57 (m, 1H), 5.14-5.09 (m, 2H), 4.23 (t, J=6.2 Hz, 2H), 4.04 (t, J=6.2 Hz, 2H), 2.14-2.09 (m, 2H), 2.06 (s, 3H),

Step 7

To a solution of compound 1g (1 g, 2.51 mmol) in methanol (10 mL) was added an aqueous solution of potassium hydroxide (1 mL, 20% purity, 489.03 μmol), and the mixture was stirred at 25° C. for 6 h. The reaction solution was poured into 10 mL of water and then the mixture was extracted with ethyl acetate (30 mL×3). The combined organic phase was washed with water (10 mL×2) and with saturated brine (10 mL×2). The organic phase was collected, dried over anhydrous sodium sulfate, and filtered. The filtrate was concentrated and the crude product was purified by column chromatography (silica gel, petroleum ether:ethyl acetate=5/1-3/1) to give compound 1b.

$^1$H NMR (400 MHz, $CDCl_3$) δ=7.15 (q, J=9.2 Hz, 1H), 7.00 (dd, J=5.2, 8.8 Hz, 1H), 6.91 (s, 1H), 6.69-6.6 (m, 2H), 6.53 (dt, J=3.0, 8.6 Hz, 1H), 5.17 (d, J=2.0 Hz, 2H), 4.22 (t, J=5.8 Hz, 2H), 3.88 (q, J=5.0 Hz, 2H), 2.49 (br s, 1H), 2.15-2.05 (m, 2H).

Step 8

To a solution of compound 1h (421 mg, 1.28 mmol) in tetrahydrofuran (400 mL) at 0° C. was added sodium hydride (135.04 mg, 60% purity, 3.38 mmol), and the mixture was stirred 0° C. for 0.5 h. A solution of p-toluenesulfonyl chloride (244.50 mg, 1.28 mmol) in tetrahydrofuran (5 mL) was added dropwise to the reaction system at 0° C., and the mixture was stirred at 25° C. for 12 h. To this reaction solution, 10 ml of water was added, and the mixture was extracted with ethyl acetate (30 ml×3). The combined organic phase was washed with water (10 ml×2) and with saturated brine (10 ml×2), dried over anhydrous sodium sulfate, and filtered. The filtrate was concentrated and the crude product was purified by preparative chromatography (petrolewn ether:ethyl acetate=3:1) to give compound Step 9

To a solution of compound 1i (53 mg, 170.82 μmol) in acetic acid (1 mL) at 80° C. was added dropwise nitric acid (1.46 mL, 60% purity, 19.51 mmol), and the mixture was stirred at 80° C. for 2 h. The reaction solution was poured into 40 mL of ice water and the mixture was adjusted to pH of 7 with saturated aqueous sodium bicarbonate. The aqueous phase was extracted with ethyl acetate (30 mL×5). The combined organic phase was washed with water (30×3) and with saturated brine (20×1), dried over anhydrous sodium sulfate, and filtered. The filtrate was concentrated to give compound 1j.

$^1$H NMR (400 MHz, $CDCl_3$) δ=7.92 (d, J=7.6 Hz, 1H), 7.14-7.10 (m, 1H), 6.76-6.73 (d, J=12.0 Hz, 1H), 6.57-6.12 (m, 1H), 5.20 (d, 1.2 Hz, 2H), 4.48-4.42 (m, 2H), 4.37-4.31 (m, 2H), 2.17-2.14 (m, 2H).

Step 10

To a solution of compound 1j (46 mg, 129.48 μmol) in ethyl acetate (10 mL) was added wet palladium on carbon (10 mg, 10% purity). The atmosphere was replaced three times with hydrogen. The mixture was stirred under hydrogen atmosphere (15 psi) at 24° C. for 12 h. The reaction solution was filtered through diatomaceous earth, and filtered. The filtrate was concentrated to give compound 1k.

$^1$H NMR (400 MHz, $CDCl_3$) δ=7.17-7.07 (m, 2H), 6.82-6.78 (m, 1H), 6.76 (d, J=11.6 Hz, 1H), 6.68 (d, J=9.0 Hz, 1H), 6.63 -6.56 (m, 1H), 5.07 (d, J=2.0 Hz, 2H 4.35-4.31 (m, 2H), 4.16-4.11 (m, 2H), 2.13-2.09 (m, 2H); LC-MS: m/z=326.1 $[M+H]^+$.

Step 11

To a solution of compound 1k (41 mg, 78.41 μmol) tetrahydrofuran (3 mL) were added compound BB-1 (26.29 mg, 78.41 μmol) and triethylamine (7.93 mg, 78.41 μmol). The mixture was stirred at 70° C. for 10 h. The reaction solution was poured into 10 ml of water, and the mixture was extracted with ethyl acetate (30 ml×5). The combined organic phase was washed with water (10 ml×3) and with saturated brine (10 ml×1), dried over anhydrous sodium sulfate, and filtered. The filtrate was concentrated and purified by preparative chromatography (petroleum ether:ethyl acetate=2/1) to give compound 1l.

$^1$H NMR (400 MHz, $CDCl_3$) δ=8.86 (s, 1H), 7.97 (s, 1H), 7.81 (d, J=8.0 Hz, 1H), 7.16-7.06 (m, 1H), 6.84 (d, J=11.6 Hz. 1H), 6.78 (m, 1H), 6.57 (br s, 1H), 5.16 (d, J=1.6 Hz, 2H), 4.36 (t, J=5.2 Hz, 2H), 4.22 (t, J=5.2 Hz, 2H), 3.91 (s, 3H), 3.90 (s, 3H), 2.11 (m, 2H), LC-MS: m/z=567.1 $[M+H]^+$.

Step 12

To a solution of compound 11 (22 mg, 28.57 μmol, 73.57% purity) in tetrahydrofuran (2 mL) and methanol (1 mL) was added a solution of lithium hydroxide monohydrate (5.99 mg, 142.85 μmol) in water (1 mL), and the mixture was stirred at 26° C. for 2 h. The reaction solution was adjusted to pH of about 6 by adding 1 mol/L dilute hydrochloric acid, and then extracted with ethyl acetate (5 mL×5). The combined organic phase was washed with water (5 mL×3). The organic phases were collected, dried over anhydrous sodium sulfate, and filtered. The filtrate was concentrated and the crude product was purified by preparative chromatography (dichloromethane:methanol=10/1) to give compound 1.

$^1$H NMR (400 MHz, DMSO-$d_6$) δ=12.05-11.76 (br s, 1H), 7.44-7.32 (m, 1 H), 7.29 (s, 1H), 7.25 (d, J=7.8 Hz, 1H), 7.16 (d, J=12.0 Hz, 1H), 7.08-7.00 (m, 1H), 5.75 (s, 1H), 5.14-5.09 (m, 1 H), 5.09-5.04 (m, 1H), 4.48 (br t, J=4.8 Hz, 2H), 4.30 (br t,=4.6 Hz, 2H), 2.01-1.91 (m, H); LC-MS: m/z=521.1 $[M+H]^+$.

Example 2

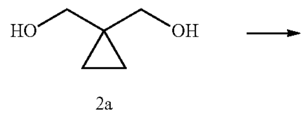

2a

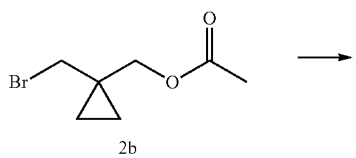

2b

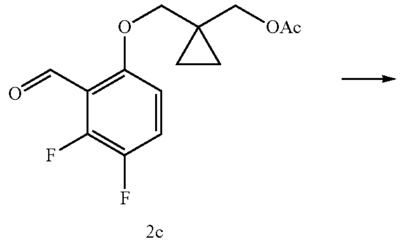

2c

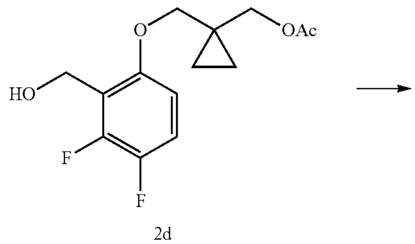

2d

-continued

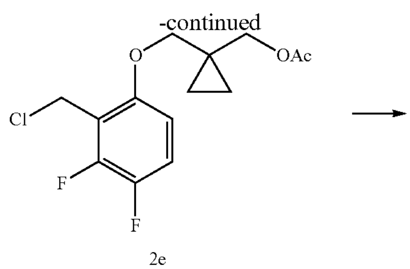

2e

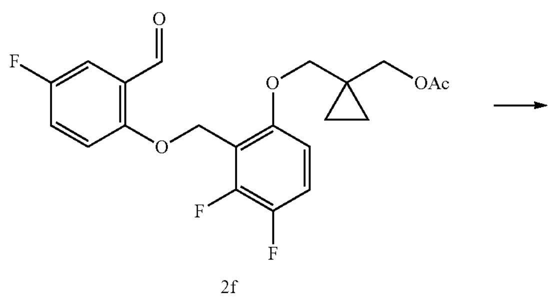

2f

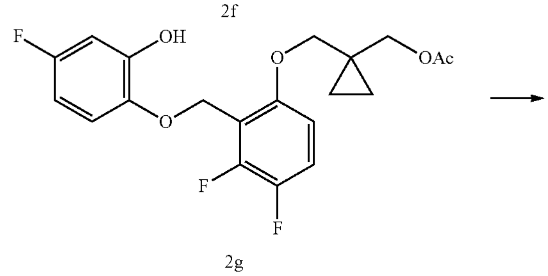

2g

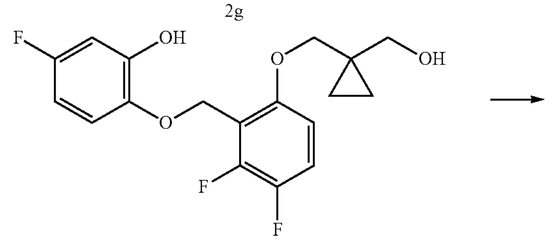

2h

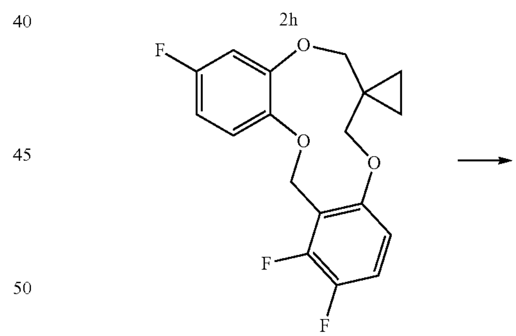

2i

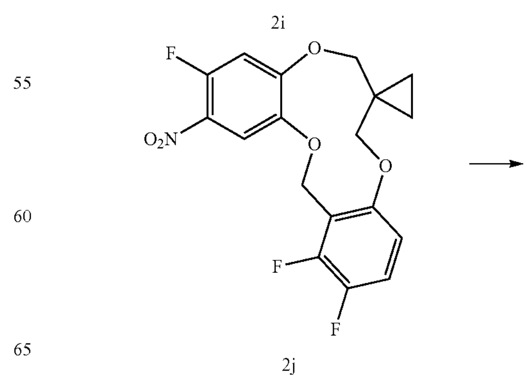

2j

-continued

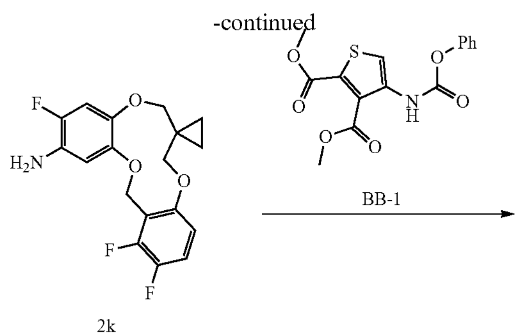

2k

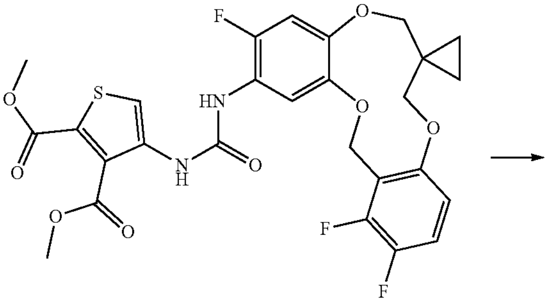

2l

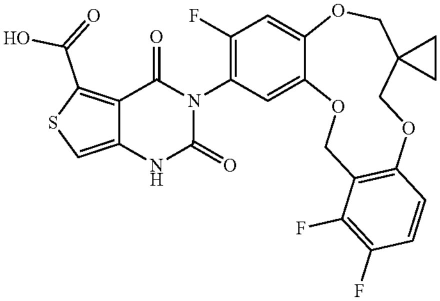

2

Step 1

To a solution of compound 2a (1,1-cyclopropyldimethanol, 10 g, 97.91 mmol) in dichloromethane (20 mL) at 0-5° C. was added dropwise a solution of hydrobromide in acetic acid (72.00 g, 293.65 mmol, 33% purity), and the mixture was stirred at 10-20° C. for 2 h, 100 mL of water was added and the mixture was extracted twice with dichloromethane, 20 mL each time. The organic phases were combined and washed twice with saturated sodium bicarbonate, 50 mL each time. The organic phases were washed with 50 mL, of saturated brine, dried over anhydrous sodium sulfate, and filtered. The filtrate was concentrated to dryness under reduced pressure to give compound 2b.

Step 2

To a solution of compound 2,3-difluoro-6-hydroxybenzaldehyde (5 g, 31.63 mmol) in N,N-dimethylformamide (50 mL) were added potassium carbonate (6.57 g, 47.55 mmol), sodium iodide (948.08 mg, 6.33 mmol), and compound 2b (9.82 g, 47.44 mmol). The mixture was stirred at 60° C. for 12 h. To the reaction solution was added 100 mL of water, and the mixture was extracted twice with ethyl acetate, 50 mL each time. The combined organic phase was washed twice with water, 50 mL each time, then washed with 50 mL of saturated brine, dried over anhydrous sodium sulfate, and filtered. The filtrate was concentrated to dryness under reduced pressure and purified by column chromatography (silica gel, 100-200 mesh, petroleum ether:ethyl acetate=1:0 to 10:1) to give compound 2c.

Step 3

To a solution of compound 2c (4.5 g, 15.83 mmol) in tetrahydrofuran (40 mL) at 0-5° C. was added a solution of sodium horohydride (0.83 g, 21.94 mmol) in water (5 mL). The reaction solution was stirred at 25° C. for 1 h. To the reaction solution was added 50 mL of water, and the mixture was extracted twice with ethyl acetate, 20 ml each time. The combined organic phase was washed with 10 ml of saturated brine, dried over anhydrous sodium sulfate, and filtered. The filtrate was concentrated to dryness under reduced pressure to give compound 2d.

Step 4

To compound 2d (4.4 g, 15.37 mmol) in dichloromethane (40 mL) at 0-5° C. were added pyridine (3.65 g, 46.11 mmol) and sulfoxide chloride (3.66 g, 30.74 mmol). The reaction was stirred at 25° C. under nitrogen for 12 h. To the reaction solution was added 50 ml of water, and the mixture was extracted twice with ethyl acetate, 50 ml each time. The organic layers were combined, washed with 20 ml of saturated sodium bicarbonate, then washed once with 30 ml of saturated aqueous sodium chloride, dried over anhydrous sodium sulfate, and filtered. The filtrate was concentrated to dryness under reduced pressure to give compound 2e.

Step 5

To a solution of compound 5-fluoro-2-hydroxybenzaldehyde (1.84 g, 13.13 mmol) and compound 2e (4.0 g, 13.13 mmol) in acetonitrile (40 mL) were added potassium carbonate (2.72 g, 19.69 mmol) and sodium iodide (196.77 mg, 1.31 mmol), and the reaction solution was stirred at 60° C. under nitrogen for 12 h. The reaction solution was filtered and the filtrate was added to 50 ml of water. The mixture was extracted twice with ethyl acetate, 50 ml each time. The organic phases were combined, washed with 50 ml of saturated brine, dried over anhydrous sodium sulfate, and filtered. The filtrate was concentrated to dryness and purified by silica gel column chromatography (100-200 mesh, petroleum ether:ethyl acetate=1:0 to 20:1) to give compound 2f.

Step 6

To compound 2f (2.2 g, 5.39 mmol) in dichloromethane (25 mL) at 0-5° C. was added m-chloroperoxybenzoic acid (1.20 g. 5.93 mmol, 85% purity), and the reaction solution was stirred at 30° C. for 36 h. The reaction solution was filtered, and the filtrate was added to 20 ml of saturated aqueous sodium bicarbonate. The mixture was extracted twice with dichloromethane, 20 ml each time. The organic phases were combined, washed twice with saturated sodium bicarbonate, 20 ml each time, then washed with 20 ml of saturated brine, dried over anhydrous sodium sulfate, and filtered. The filtrate was concentrated to dryness to give compound 2g.

Step 7

To compound 2g (2.2 g, 5.18 mmol) in methanol (10 mL) and water (2 mL) was added potassium carbonate (2.15 g, 15.55 mmol). The reaction solution was stirred at 40° C. for 2 h. To the reaction solution was added 30 ml of water, and the mixture was extracted twice with ethyl acetate, 20 ml each time. The organic layers were combined, washed with 30 ml of saturated aqueous sodium chloride, dried over anhydrous sodium sulfate, and filtered. The filtrate was concentrated to dryness under reduced pressure and purified by silica gel column chromatography (100-200 mesh, petroleum ether:ethyl acetate=20:1 to 5:1) to give compound 2h.

Step 8

To a solution of compound 2h (1,63 g, 4.60 mmol) in tetrahydrofuran (30 mL) at 0° C. were added sodium hydride (552.04 mg, 13.80 mmol, 60% purity) and p-toluenesulfonyl chloride (877.06 mg, 4.60 mmol), and the reaction was stirred at 35° C. under nitrogen for 60 h. To the reaction solution were added 2 mL of saturated aqueous ammonium chloride and 10 mL of water, and the mixture was extracted twice with ethyl acetate, 10 inL each time. The organic phases were combined, washed with 10 mL of saturated brine, dried over anhydrous sodium sulfate, and filtered. The filtrate was concentrated under reduced pressure and purified by silica gel column chromatography (100-200 mesh, petroleum ether:ethyl acetate=1:0 to 10:1) to give compound 2i.

$^1$H NMR (400 MHz, $CDCl_3$) δ=7.19-7.06 (m, 2H), 6.75-6.67 (m, 3H), 5.17 (d, J=1.6 Hz, 2H), 4.13 (s, 2H), 3.98 (s, 2H), 0.72 (s, 4H).

Step 9

To a solution of compound 21 (360 mg, 1.07 mmol) in acetic acid (3 mL) at 60° C. was added dropwise nitric acid (518.84 mg, 5.35 mmol, 65% purity), and the reaction was stirred at 60° C. for 2 h. 10 ml of water was added to the reaction solution. Solid was precipitated, and filtered. The filter cake was dried under reduced pressure and purified by silica gel column chromatography (100-200 mesh, petroleum ether:ethyl acetate=10:1 to 5:1) to give compound 2j.

Step 10

To a solution of compound 2j (200 mg, 524.52 μmol) in ethanol (4 mL) and water (0.8 mL) at 79° C. were added ammonium chloride (140.29 mg, 2.62 mmol) and reduced iron powder (146.46 mg, 2.62 mmol), and the reaction was stirred at 79° C. for 3 h. To the reaction solution was added water (10 mL) and the mixture was extracted twice with ethyl acetate, 10 mL each time. The organic phases were combined, washed with 10 mL of saturated brine, dried over anhydrous sodium sulfate, and filtered. The filtrate was concentrated under reduced pressure and purified by silica gel column chromatography (100-200 mesh, petroleum ether:ethyl acetate=1:0 to 5:1) to give compound 2k.

LC-MS: m/z=352.1 $[M+H]^+$.

Step 11

To a solution of compound BB-1 (143.17 mg, 426.96 μmol) and compound 2k (150 mg, 426.96 μmol) in tetrahydrofuran (5 mL) was added triethylamine (43.2 mg, 426.96 panol), and the reaction was stirred at 35° C. for 60 h. The reaction solution was concentrated to dryness under reduced pressure and purified by silica gel column chromatography (100-200 mesh, petroleum ether:ethyl acetate=20:1 to 5:1) to give compound 2l.

LC-MS: m/z=593.2 $[M+H]^+$.

Step 12

To compound 2l (100 mg, 168.77 μmol) in tetrahydrofuran (2 mL) and methanol (2 mL) was added a solution of lithium hydroxide monohydrate (35.41 mg, 843.83 μmol) in water (2 mL), and the reaction was stirred at 20° C. for 2 h. The reaction solution was adjusted to pH 4-5 with 1 mole per liter of hydrochloric acid. Solid was precipitated, and filtered. The filter cake was concentrated to dryness under reduced pressure. Ethyl acetate (5 mL) and petroleum ether (25 mL) were added. The mixture was slurried at 20° C. for 30 min., and then filtered, The filter cake was dried under reduced pressure to give compound 2.

$^1$H NMR (400 MHz, DMSO-$d_6$) δ=11.72 (br s, 1H), 7.38 (q, J=9.6 Hz, 1H), 7.25 (hr d, J=8.0 Hz, 1H), 7.16-7.03 (m, 2H), 6.99 (br s, 1H), 5.10 (br s, 2H), 4.28 (s, 2H), 4.10-4.03 (m, 2H), 0.68-0.60 (m, 4H); LC-MS: m/z=547.1 $[M+H]^+$.

Example 3

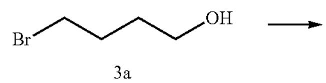

3a

-continued

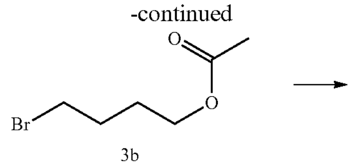

3b

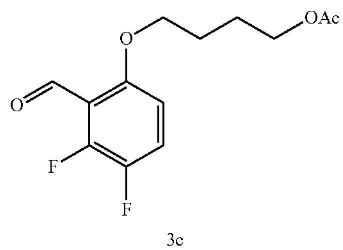

3c

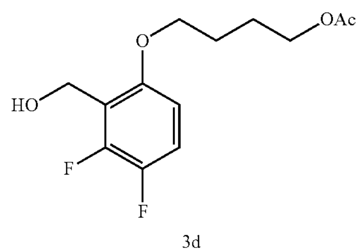

3d

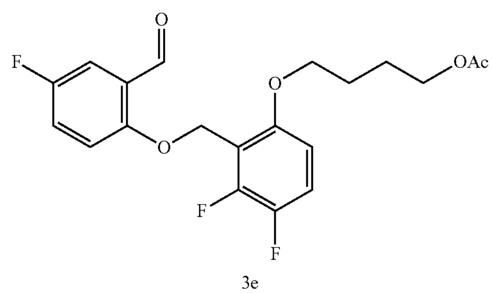

3e

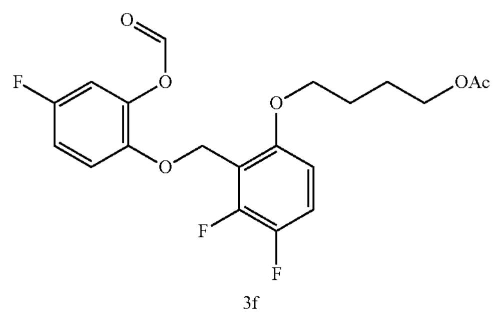

3f

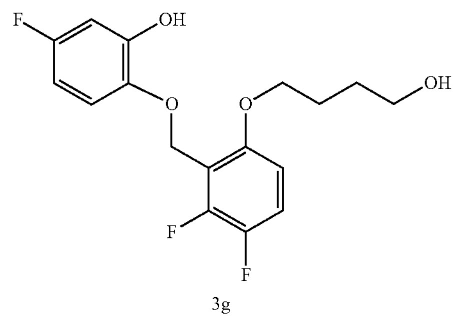

3g

-continued

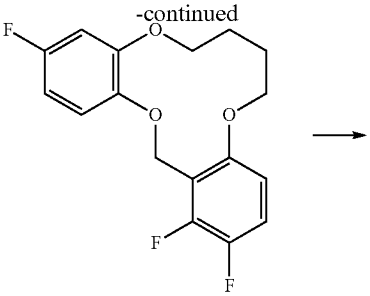

3h

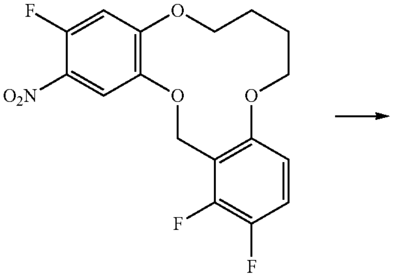

3i

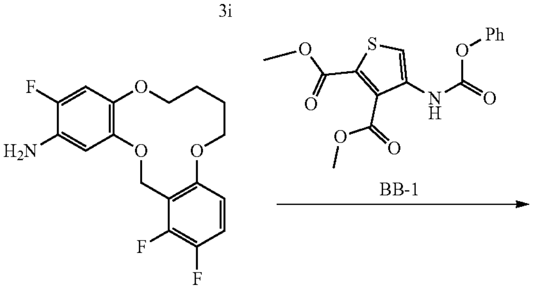

3j

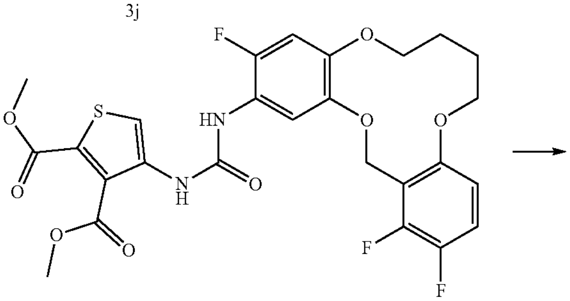

3k

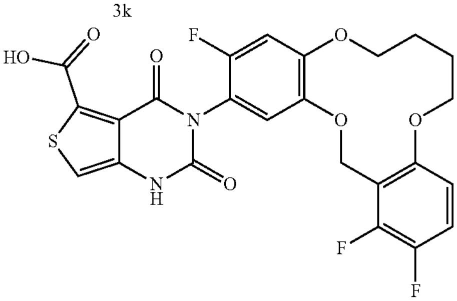

3

Step 1

To a solution of compound 3a (4-promo-1-butanol, 10 g, 65.35 mmol) dichloromethane (100 mL) at 0-5° C. were added triethylamine (9.92 g, 98.03 mmol) and acetic anhydride (7.34 g, 71.89 mmol), and the mixture was Stirred at 25° C. under nitrogen for 12 h. To the reaction solution was added 100 ml of water, and the mixture was extracted twice with dichloromethane, 100 ml each time. The combined organic phase was washed with 100 ml of saturated brine, dried over anhydrous sodium sulfate, and filtered. The filtrate was concentrated under reduced pressure to give compound 3b.

Step 2

To a solution of compound 2,3-difluoro-6-hydroxymethylbenzaldehyde (4 g, 25.30 mmol) in N,N-dimethyltbrmamide (40 mL) were added potassium carbonate (5.26 g, 38.04 mmol.), sodium iodide (758.45 mg, 5.06 mmol), and compound 3b (6.42 g, 32.89 mmnol). The mixture was stirred at 60° C. for 12 h. To the reaction solution was added 100 ml of water, and the mixture was extracted—twice with ethyl acetate, 50 ml each time. The combined organic phase was washed twice with water, 50 ml each time, then washed with 50 ml of saturated brine, dried over anhydrous sodium sulfate, and filtered. The filtrate was concentrated under reduced pressure to give compound 3c.

Step 3

To a solution of compound 3c (5 g, 18.37 mmol) in tetrahvdrofuran (30 mL) at 0-5° C. was added a solution of sodium borohydride (800 mg, 21.15 mmol) in water (3 mL). The reaction solution was stirred at 25° C. for 1 h. To the reaction solution was added 50 ml of water, and the mixture was extracted twice with ethyl acetate, 20 ml each time. The combined. organic phase was washed with 10 ml of saturated brine, dried over anhydrous sodium sulfate, and filtered, The filtrate was concentrated under reduced pressure to give compound 3d.

Step 4

To compound 5-fluoro-2-hydroxybenzaldehyde (2.66 g, 18.96 mmol) and compound 3d (5.2 g, 18.96 mmol) in tetrahydrofuran (50 mL) at 0-5° C. were added tri-n-butylphosphine (5.75 g, 28.44 mmol) and azodicarbonyldipiperidine (7.18 g, 28.44 mmol). The reaction was stirred at 25° C. under nitrogen for 12 h. The reaction solution was filtered and the filtrate was added to 50 mL of water. The mixture was extracted twice with ethyl acetate, 50 mL each time. The organic layers were combined, washed once with 50 mL of saturated aqueous sodium chloride, dried over anhydrous sodium sulfate, and filtered. The filtrate was concentrated under reduced pressure and purified by silica gel column chromatography (100-200 mesh, petroleum ether:ethyl acetate=1:0 to 20:1) to give compound 3e.

Step 5

To a solution of compound 3e (2.6 g, 6.56 (nmol) in dichloromethane (30 mL) was added m-chloroperoxybenzoic acid (1.33 g, 6.56 mmol, 85% purity), and the reaction solution was stirred at 25° C. for 12 h. The reaction solution was filtered, and the filtrate was added to 30 ml of sodium bicarbonate. The mixture was extracted twice with dichloromethane, 10 ml each time. The organic phases were combined, washed three times with saturated sodium bicarbonate, 30 ml each time, then washed with saturated brine (10 ml), dried over anhydrous sodium sulfate, and filtered. The filtrate was concentrated to dryness and purified by silica gel column chromatography (100-200 mesh, petroleum ether:ethyl acetate=1:0 to 10:1) to give compound 3f.

Step 6

To compound 3f (1.5 g. 3.90 mmol) in methanol (2 mL) and water (2 mL) was added potassium carbonate (1.08 g, 7.81 mmol). The reaction solution was stirred at 25° C. for 12 hours. To the reaction solution was added 30 mL of water, and the mixture was extracted twice with ethyl acetate, 20 mL each time. The organic layers were combined, washed with 30 mL of saturated aqueous sodium chloride, dried over anhydrous sodium sulfate, and filtered. The filtrate was concentrated under reduced pressure to give compound 3g.

$^1$H NMR (400 MHz, $CDCl_3$) δ=7.14 (q, J=9.2 Hz, 1H), 7.02-7.0 (m, 1H), 6.66-6.45 m, 2H), 6.63-6.53 (m, 1H), 5.11 (d, J=1.8 Hz, 2H), 4.07 (t, J=6.0 Hz, 2H), 3.70 (t, J=6.0 Hz, 2H), 1.97-1.89 (m, 2H), 1.76-1.70 (m, 2H).

Step 7

To a solution of compound 3g (800 mg, 2.34 mmol) in tetrahydrofuran (20 mL) at 0° C. were added sodium hydride (233.71 mg, 5.84 mmol, 60% purity) and p-toluenesulfonyl chloride (445.56 mg, 2.34 μmol), and the reaction was stirred at 25° C. under nitrogen for 60 h. To the reaction solution were added 2 mL of saturated aqueous ammonium chloride and 10 mL of water, and the mixture was extracted twice with ethyl acetate, 10 mL each time. The organic phases were combined, washed with 10 mL of saturated brine, dried over anhydrous sodium sulfate, and filtered. The filtrate was concentrated under reduced pressure and purified by silica gel column chromatography (100-200 mesh, petroleum ether:ethyl acetate=1:0 to 10:1) to give compound 3h.

$^1$H NMR (400 MHz, $CDCl_3$) δ=7.17-7.10 (m, 2H), 6.70-6.62 (m, 3H), 5.04 (d, J=2.0 Hz, 2H), 4.16-4.13 (m, 4H) 2.10-2.04 (m, 4H).

Step 8

To a solution of compound 3h (100 mg, 308.36 μmol) in acetic acid (1 mL) at 0-5° C. was added nitric acid (149.46 mg, 1.54 mmol, 65% purity), and the reaction was stirred at 60° C. for 1 h. To the reaction solution was added 10 ml of water. Solid was precipitated, and filtered. The filter cake was dried under reduced pressure, and then ethyl acetate (1 ml) and petroleum ether (10 ml) were added. The mixture was slurried at 25° C. for 30 min, and filtered. The filter cake was dried under reduced pressure to give compound 3i.

Step 9

To a solution of compound 3i (1100 mg, 270.79 μmol) in ethyl acetate (10 mL) was added wet palladium on carbon (10 mg, 10% purity, 50% water), and the reaction was stirred at 25° C. under 15 psi hydrogen for 7 h. The reaction solution was filtered and the filtrate was concentrated to give compound 3j.

LC-MS: m/z=340.1 $[M+H]^+$.

Step 10

To a solution of compound BB-1 (69.18 mg, 206.30 μmol) and compound 3j (70 mg, 206,30 μmol) tetrahydrofuran (5 mL) was added triethylamine (41.75 mg, 412.60 μmol), and the reaction was stirred at 35° C. for 36 h. The reaction solution was concentrated to dryness under reduced pressure, and ethyl acetate (2 mL) and petroleum ether (20 mL) were added. The mixture was slurried at 25° C. for 30 min, and filtered. The filter cake was dried under reduced pressure to give compound 3k.

LC-MS: m/z=581.3 $[M+H]^+$.

Step 11

To a solution of compound 3k (150 mg, 258.39 μmol) in tetrahydrofuran (1 mL). methanol (1 mL) and water (1 mL) was added lithium hydroxide monohydrate (65.06 mg, 1.55 mmol), and the reaction was stirred at 25° C. for 2 h. The reaction solution was adjusted to pH 4-5 with 1 mol per liter of hydrochloric acid, and stirred at 25° C. for 10 min. Solid was precipitated, and filtered. The filter cake was concentrated to dryness under reduced pressure, and ethyl acetate (5 mL) and petroleum ether (20 mL) were added. The mixture was slurried at 25° C. for 30 min, filtered, dried under reduced pressure, and then purified by preparative high performance liquid chromatography (column: 3_Phenomenex Luna $C_{18\ 75*30}$ min*3 μm; mobile phase: [water (0.05% hydrochloric acid)-acetonitrile]; acetonitrile %: 47%-67%) to give compound 3.

$^1$H NMR (400 MHz, DMSO-$d_6$) δ=12.03 (br s, 1H), 7.44 (q, J=9.6 Hz, 1H), 7.39-7.35 (m, 2H), 7.17 (d, 11.2 Hz, 1H), 6.95-6.88 (m, 1H), 4.99 (s, 2H), 4.17-4.14 (m, 4H), 1.96 (br s, 4H); LC-MS: m/z=535.1 $[M+H]^+$.

Example 4

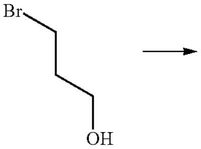

4a

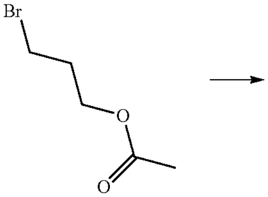

4b

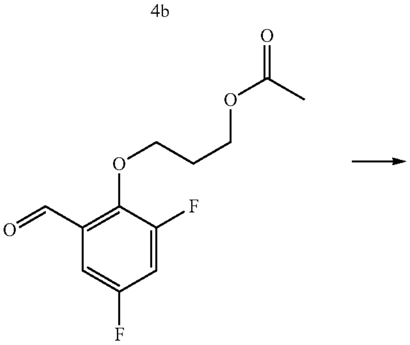

4c

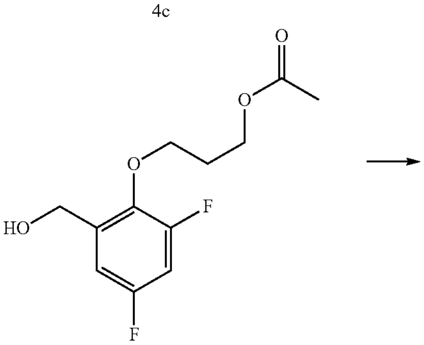

4d

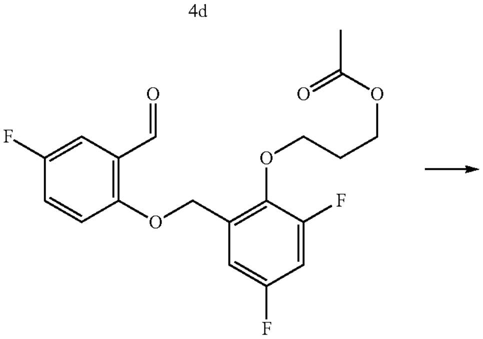

4e

-continued

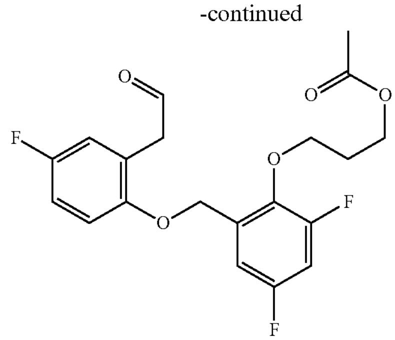

4f

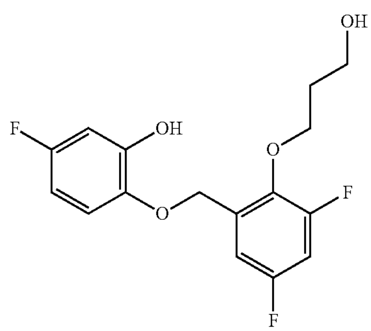

4g

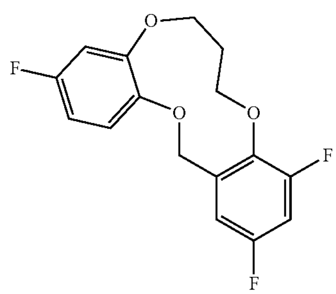

4h

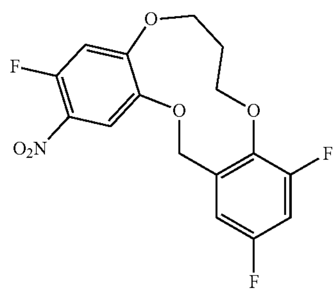

4i

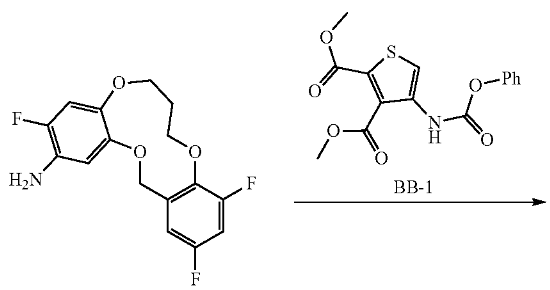

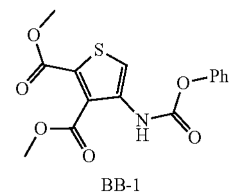

BB-1

4j

-continued

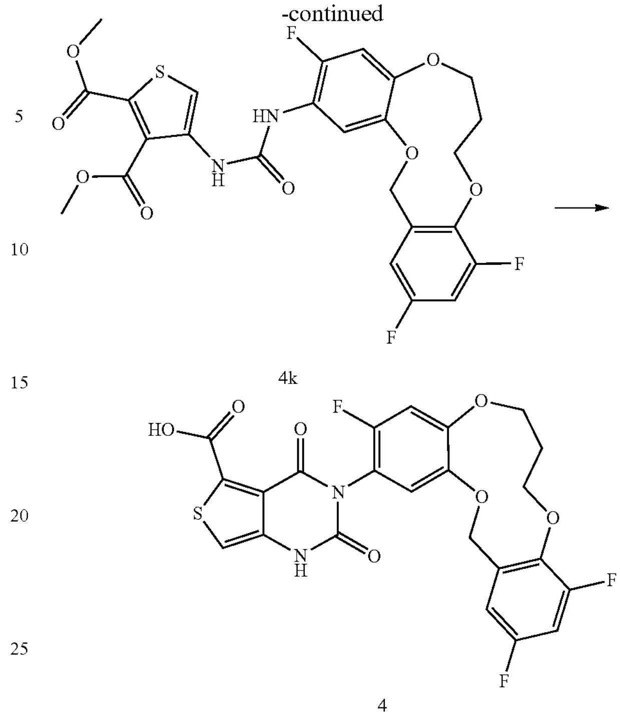

4k

4

Step 1

Compound 4a (3-bromopropanol, 12 g, 86.34 mmol) was dissolved in 60 mL of dichloromethane solution, and triethylamine (13.10 g, 129.50 μmol) was added. The reaction solution was stirred at 25° C. for 20 min, and then cooled to 0° C. Then acetic anhydride (10.58 g, 103.60 mmol) was dissolved in 10 mL of dichloromethane and the solution was added dropwise to the reaction solution. The reaction solution was stirred at 25° C. for 12 h. The reaction solution was poured into 50 ml of water and adjusted to pH 3-5 with 1 N dilute hydrochloric acid. The organic phase was washed three times with water. 30 ml each time. The organic phase was dried over anhydrous sodium sulfate, and filtered. The filtrate was concentrated to give compound 4b.

$^1$H NMR (400 MHz, $CDCl_3$) δ=4.21 (t, J=6.4 Hz, 2H), 3.47 (t, J=6.4 Hz, 2H), 2.25-2.13 (m, 2H), 2.07 (s, 3H).

Step 2

Compound 3,5-difluoro-2-hydroxy-benzaldehyde (7.5 g, 47.44 mmol) and compound 40 (11.16 g, 61.67 mmol) were dissolved in 100 ml of N,N-dimethylformamide, and then potassium carbonate (13.11 g, 94.88 mmol) was added. The mixture was then heated to 75° C. and stirred at 75° C. for 12 hours. The reaction solution was cooled to 25° C., and poured into 200 mL of water. The mixture was extracted with ethyl acetate three times, 100 mL each time. The organic phases were combined and washed with water four times, 100 mL each time. The organic phase was concentrated and the crude product was purified by silica gel column (silica gel, 100-200 mesh, petroleum ether:ethyl acetate=1/0-20/1) to give compound 4c.

Step 3

Compound 4c (12 g, 46.47 mmol) was dissolved in 100 mL of tetrahydrofuran and 10 mL of water, and the solution was cooled to 0° C. Sodium borohydride (2.11 g, 55.77 mmol) was added in batches and then the mixture was stirred at 25° C. for 3 h. The reaction was quenched with 1 mol/L dilute hydrochloric acid to a pH of about 6, and then extracted twice with ethyl acetate, 50 mL each time. The organic phases were combined, washed once with 100 mL of saturated brine, dried over anhydrous sodium sulfate, and filtered. The filtrate was concentrated to give compound 4d.

Step 4

Compound 4d (8 g, 30.74 mmol), 5-fluorosalicylaldehyde (5.6 g, 39.96 mmol), and tri-n-butylphosphine (12.44 g, 61.48 mmol) were dissolved in 50 mL of tetrahydrofuran and the solution was cooled to 0° C. Then azodicarbonyldipiperidine (15.51 g, 61.48 mmol) was added in batches and the mixture was stirred at 25° C. under nitrogen for 12 h. The reaction solution was poured into 50 mL of water and the mixture was extracted twice with ethyl acetate, 50 mL each time. The organic phases were combined and concentrated. The crude product was purified by silica gel column (silica gel, 100-200 mesh, petroleum ether:ethyl acetate=1/0-20/1) to give compound 4e.

Step 5

Compound 4e (6.5 g, 17.00 mmol) was dissolved in 55 mL of dichloromethane solution, and m-chloroperoxybenzoic acid (4.83 g, 2380 mmol, purity: 85%) was added. The mixture was then heated to 35° C. and stirred at 35° C. for 12 hours. The reaction solution was cooled to 25° C., and filtered. The filtrate was washed twice with water, 25 mL each time, then twice with saturated sodium bicarbonate, 20 mL each time, and twice with saturated sodium sulfite solution, 30 mL each time. The organic phase was concentrated and the crude product was purified by silica gel column (silica gel, 100-200 mesh, petroleum ether:ethyl acetate=1/0-20/1) to give compound 4f.

Step 6

Compound 4f (5 g, 12.55 mmol) was dissolved in 50 mL of methanol and 10 mL of water, and potassium carbonate (5.2 g, 37.66 mmol) was added. The mixture was then stirred at 25° C. for 12 h. The mixture was filtered, and the filtrate was concentrated. The crude product was diluted with 20 ml of ethyl acetate, washed with 20 ml of saturated brine, dried over anhydrous sodium sulfate, and filtered. The filtrate was concentrated to give compound 4g.

Step 7

Compound 4g (1.63 g, 4.97 mmol) was dissolved in 20 mL of tetrahydrofuran, and the solution was cooled to 0° C. Sodium hydride (595.77 mg, 60% purity, 14.90 mmol) was added and the mixture was then stirred at 0° C. for 0.5 h. Then p-toluenesulfonyl chloride (946.61 mg, 4.97 mmol) was added, and the mixture was heated to 50° C. and stirred at 50° C. for 24 hours. The reaction solution was cooled to 25° C., and then quenched by adding 20 mL of saturated ammoniutn chloride solution, The mixture was extracted once with 20 mL of ethyl acetate, and concentrated. The crude product was purified by silica gel column (silica gel, 100-200 mesh, petroleum ether:ethyl acetate=1/0-20/1) to give compound 4k.

Step 8

Compound 4k (130 mg, 418.99 μmol ) was dissolved in 2 mL of acetic acid, and nitric acid (81.24 mg, 837.99 μmol, purity: 65%) was added. The mixture was then heated to 65° C. and stirred at 65° C. for 1 hour. The reaction solution was cooled to 25° C., and poured into 5 mL of water. The mixture was extracted twice with ethyl acetate, 5 mL each time. The organic phases were combined, washed twice with saturated sodium bicarbonate solution, 5 mL each time, dried over anhydrous sodium sulfate, and filtered. The filtrate was concentrated to give compound 4i.

Step 9

Compound 4i (110 mg, 309.63 μmol) was dissolved in 3 mL of ethyl acetate, and palladium on carbon (50 mg, purity: 10%) was added under nitrogen. The atmosphere was replaced 3 times with hydrogen and the mixture was stirred at 25° C. under hydrogen (15 psi) atmosphere for 12 h. The reaction solution was filtered, and the filtrate was concentrated to give compound 4j, which was used directly in the next step.

LC-MS: m/z=326.1 $[M+H]^+$.

Step 10

Compound 4j (100 mg, 307.43 μmol) and compound BB-1 (103.09 mg, 307.43 μmol) were dissolved in 5 mL of tetrahydrofuran solution, and triethylamine (31.11 mg, 307.43 μmol) was added. The mixture was then heated to 70° C. and then stirred at 70° C. for 12 h. The reaction solution was concentrated and the crude product was purified by thin layer chromatography plate (petroleum ether: ethyl acetate=3:1) to give compound 4k.

LC-MS:m/z=567.1$[M+H]^+$.

Step 11

Compound 4k (80 mg, 141.22 μmol) was dissolved in 3 mL of tetrahydrofuran and 0.5 mL of methanol. Lithium hydroxide monohydrate (35.56 mg. 847.30 μmol) was dissolved in 0.5 mL of water, and the solution was added dropwise to the reaction solution. The mixture was then stirred at 25° C. for 2 h. The mixture was adjusted to pH 2-3 with 1 mol/L dilute hydrochloric acid and then diluted with 3 mL of water. The mixture was extracted three times with ethyl acetate, 3 mL each time. The organic phases were combined, washed once with 5 mL of saturated brine, dried over anhydrous sodium sulfate, and filtered. The filtrate was concentrated to give compound 4.

$^1$H NMR (400 MHz, DMSO-$d_6$) δ=14.45 (br s, 1H), 12.03 (s, 1H), 7.47-7.35 (m, 3H), 7.26 (br d, 10.4 Hz, 1H), 7.18 (br d, J=8.4 Hz, 1H), 5.09 (s, 2H), 4.37 (br s, 2H), 4.21 (br s, 2H), 2.09 (br s, 2H); LC-MS: m/z=521.1 $[M+H]^+$.

Biological Assay Data

Assay Example 1. Assay of the Activity of the Compounds of the Present Disclosure on Human Gonadotropin-Releasing Hormone Receptor Objective of assay: to detect the inhibitory activity of assay compounds on gonadotropin-releasing hormone receptor at the cellular level using FLIPR detection technology.

Main Materials and Sources in Assay:

Fluo-4 Direct™ Kit—Invitrogen-F10471

384-well Poly-Lysine-Coated Cell Plate—Greiner-781946

384-well Compound Plate—Greiner-781280

ECHO (Sonic Pipetting System) for Compound Preparation—Labcyte

FLIPR (Fluorescence Imaging Plate Reader)—Molecular Devices

Assay Procedure:

GnRH/HEK293 (human embryonic kidney cell 293) cultured cells in the logarithmic growth phase were washed with DPBS (Dulbecco's phosphate buffered saline) buffer, and an appropriate amount of 0.05% EDTA (ethylenediaminetetraacetic acid)-trypsin was added. The cells were placed in a carbon dioxide incubator at 37° C. for digestion for 1-2 minutes, and then removed from the incubator. A medium was added to the cells to terminate the digestion. Cells were dispersed by repeated pipetting and harvested by centrifugation. The cells were seeded into a 384-well Poly-Lysine-Coated. Cell Plate at a density of 20,000 cells per well. 20 μL, and incubated overnight in a 5% $CO_2$, 37° C. incubator.

On the next day, 20 μL, of 2×Fluo-4Direct™ buffer was added to each well, and the plate was incubated in a 5% $CO_2$, 37° C. incubator for 50 minutes. The cells were placed at room temperature for 10 minutes. 0.2 nM Leuprolide acetate was diluted to 10 concentrations by 4-fold serial dilution in ECHO, and 900 nL of that was transferred to the compound plate. 30 μL of FLIPR buffered saline was added to the compound plate, and the plate was centrifuged at 1000 rpm for 1 min. The software of the FLIPR instrument was run, and 10 μL of assay buffer salt solution was added according to the set program. The fluorescence signal was read. Then 10 μL of the reference compound as an agonist was added, and the fluorescent signal was read. $EC_{50}$ was calculated, and the agonist with a concentration of 6×$EC_{50}$ was prepared.

2 mM assay compounds and an appropriate concentration of reference compound were serially diluted 4-fold to 10 concentrations in ECHO, and 900 nL of that was transferred to a compound plate. 30 μL of FLIPR buffered saline was added to the compound plate, and the plate was centrifuged at 1000 rpm for 1 min. The software of the HIM instalment was run, and 10 μL of assay and reference compounds were added to the cell plate according to the set program. The fluorescent signal was read. Then 10 μL of agonist with a concentration of 6×$EC_{50}$ was added to the cell plate and the fluorescent signal was read.

$IC_{50}$ of the compound to inhibit the calcium flow of gonadotropin-releasing hormone receptor, i.e., the drug concentration when the $Ca^{2+}$ flow was inhibited by half in the cells stably expressing the GnRH receptor, was calculated. The $IC_{50}$ of the drug was calculated by GraphPad Prism 5.0 software.

Assay Results:

The inhibitory activity of the compounds of the present disclosure on the human gonadotropin-releasing hormone receptor was determined by the above assay method, and the determined $IC_{50}$ is shown in Table 1:

TABLE 1

$IC_{50}$ of the compounds of the present disclosure on inhibiting the activity of human gonadotropin-releasing hormone receptor

| Compound No. | $IC_{50}$ (nM) |
|---|---|
| Compound 1 | 3.2 |
| Compound 2 | 9.2 |
| Compound 3 | 10.1 |
| Compound 4 | 18.0 |

Conclusion: The compounds of the present disclosure have a significant inhibitory effect on a human gonadotropin-releasing hormone receptor.

Assay Example 2. In Vivo Efficacy Evaluation

Objective of assay: To evaluate the efficacy of the compound of the present disclosure in a mouse model of endometriosis.

Assay Scheme:

2.1 Main Reagents and Consumables

C57BL6/J female mice, Vernier calipers (ARZ-1331), 8-0 sutures, and stereomicroscope.

2.2 Assay Step

Animal estrous cycle detection in 8-week-old C57BL6/J female mice: Through vaginal smear observation, mice that met the specific estrous cycle on the day of the assay were selected according to the actual smear results because the entire estrous cycle was about 4 days.

Modeling: The uterine horns of donor mice in an estrous cycle were excised, and opened longitudinally. The excised biopsies were cut to a size of 2×2 mm. Recipient mice were anesthetized with isoflurane gas, and a 1 cm incision was made along the midline to expose the abdominal cavity. Endometriotic mice: four uterine fragments of donors were sutured to the peritoneal wall of mice in an estrous cycle; sham-operated mice: abdominal fat fragments of similar size were sutured. The grafted tissue as well as the abdominal muscle and skin were sutured using 8-0 black silk thread. Sham group (sham-operation group): the abdominal cavity of each mouse in the Sham group was opened to transplant fat fragments, and the rest of the steps were the same.

After 4 weeks of modelmg, a second laparotomy was performed, and the ectopic lesion volume ($V_1$) was measured using a vernier caliper and calculated to determine the success of the modeling. Twelve mice with relatively uniform $V_1$ were selected and divided into 2 groups with 6 nice in each group: Vehicle (vehicle control group) and drug group.

Sham group (sham-operation group, 6 animals): normal feeding; Vehicle group (vehicle control group, 6 animals); vehicle was intragastrically administered once a day for 8 consecutive weeks. The vehicle was 10% DMAC+10% solutol+80% normal saline; Compound group (6 animals): 100 mpk was intragastrically administered at 10:00 a.m. every day for 8 consecutive weeks, and the vehicle was 10% DMAC 10% solutol+80% normal saline.

After 8 weeks of administration, samples were obtained from the mice: the ectopic lesion volume ($V_2$) was measured using a vernier caliper and calculated. The inhibition rate was calculated using a calculation formula of: ectopic lesion volume V=π/6×length×width×height, wherein length represents the length of an ectopic lesion, width represents the width of an ectopic lesion, and height represents the height of an ectopic lesion;

$$\text{Inhibition rate} = \left(1 - \frac{V_2 \text{ in compound administration} - V_1 \text{ in compound administration}}{V_2 \text{ in vehicle control} - V_1 \text{ in vehicle control}}\right) \times 100\%.$$

Assay results: The assay results are shown in Table 2.

TABLE 2

Inhibitory results of the compound of the present disclosure in a mouse model of endometriosis

| | Volume of endometriotic lesion in mice ($mm^3$, Mean ± SD, n = 6) | | Inhibition |
|---|---|---|---|
| Group | $V_1$ | $V_2$ | rate |
| Sham | 0 ± 0 | 0 ± 0 | — |
| Vehicle | 9.75 ± 1.61 | 51.39 ± 16.73 | — |
| Compound 1 | 9.89 ± 1.51 | 6.78 ± 4.46 | 107.5% |

Assay conclusion: the compound of the present disclosure can significantly inhibit the increase of the volume of the endometriotic lesion in mice, and has excellent efficacy in vivo.

Assay Example 3. Pharmacokinetic Evaluation

Objective of assay: To study the in vivo pharmacokinetic properties of the compound of the present disclosure in mice.

Assay Scheme:

Each assay compound was mixed with DMAC respectively, and vortexed for 2 minutes. The solution of the assay compound in DMAC was mixed and vortexed for 2 minutes to prepare a clear solution of 10 mg/mL. 0.0600 mL of 10 mg/mL solution was added to 0.300 mL of Solutol, and the mixture was vortexed for 2 minutes. Then 2.400 mL of normal saline was added, and the mixture was vortexed for 2 minutes to obtain a clear solution of 0.2 mg/mL, which was used for administration in PO group, 0.500 mL of the solution for administration in PO group was vortexed for 2 minutes, and 0.0500 mL of DMAC was added. The mixture was vortexed for 2 minutes, and then 0.0500 mL of solutol was added. The mixture was vortexed for 2 minutes, and finally 0.400 mL of normal saline was added. The mixture was vortexed for two minutes to give a clear solution of 0.1 mg/mL, which was filtered through a microporous membrane to give a solution for administration in injection (IV) group.

Four male CD-1 mice were divided into two groups. The animals in the first group were administered intravenously once at a dose of 0.5 mg/kg, wherein the vehicle was 10% DMAC/10% Solutol/80% normal saline, and the administration volume was 5 mL/kg. The animals in the second group were administered orally 2 mg/kg of the assay compound by oral gavage, wherein the oral vehicle was 10% DMAC/10% Solutol/80% normal saline, and the oral volume was 10 mL/kg. Whole blood was collected at 0.033 (IV injection only), 0.083, 0.25, 0.5, 1, 2, 4 and 12 hours post-dose. The whole blood was centrifuged at 3200 g at 2-8° C. for 10 min to obtain plasma. The concentration of the assay compound in plasma was determined by ILC/MS/MS method, and the pharmacokinetic parameters were calculated by Phoenix WinNonlin software.

Assay Results:

The assay results are shown in Table 3. The parameters have the following meanings: IV: intravenous injection; PO: oral administration; $C_0$: initial plasma drug concentration; $C_{max}$: maximum drug concentration in systemic circulation; $T_{max}$: time required to reach $C_{max}$; $T_{1/2}$: half-life; $V_{dss}$: apparent volume of distribution; Cl: clearance rate; $AUC_{0-last}$: area under the drug-time curve.

TABLE 3

Pharmacokinetic (PK) assay results of compound 1 in plasma

| PK parameter | IV (0.5 mg/kg) | PO (2 mg/kg) |
|---|---|---|
| $C_0$ (nmol/L) | 13513 | — |
| $C_{max}$ (nmol/L) | — | 25800 |
| $T_{max}$ (h) | — | 0.500 |
| $T_{1/2}$ (h) | 5.66 | 5.03 |
| $V_{dss}$ (L/kg) | 0.159 | — |
| Cl (mL/min/kg) | 0.332 | — |
| $AUC_{0-last}$ (h * nmol/L) | 48307 | 142824 |
| Bioavailability (%) | — | 95.3 |

"—" means not assayed or no data available.

Conclusion: The compound of the present disclosure has high exposure in plasma, low clearance rate, long half-life, and high oral bioavailability, and exhibits excellent pharmacokinetic properties.

What is claimed is:

1. A compound represented by formula (II) or a pharmaceutically acceptable salt thereof, (II)

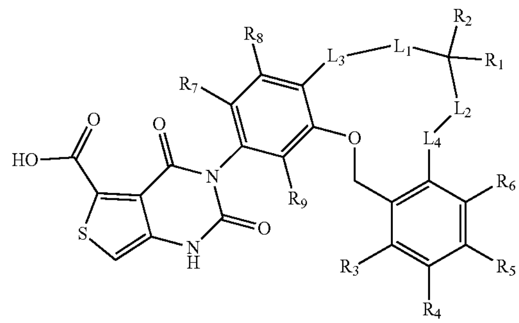

wherein $L_1$ and $L_2$ are each independently selected from $-(CH_2)n-$;

$L_3$ and $L_4$ are each independently selected from $-CH_2-$, $-CH{=}CH-$, $-O-$ and $-S-$;

$R_1$ and $R_2$ are each independently selected from H, OH, F, Cl, $C_{1-3}$ alkyl and $C_{1-3}$ alkoxy, wherein the $C_{1-3}$ alkyl and $C_{1-3}$ alkoxy are each independently optionally substituted with 1, 2 or 3 $R_a$;

alternatively, $R_1$ and $R_2$ are taken together with the atom to which they are commonly attached to form a $C_{3-6}$ cycloalkyl or 4- to 6-membered heterocycloalkyl, wherein the $C_{3-6}$ cycloalkyl or 4- to 6-membered heterocycloalkyl is optionally substituted with 1, 2 or 3 $R_b$;

$R_3$, $R_4$, $R_5$, $R_6$, $R_7$, $R_8$ and $R_9$ are each independently selected from H, F, Cl, Br, I, OH, $NH_2$, CN, $C_{1-3}$ alkyl, $C_{1-3}$ alkoxy and $C_{3-6}$ cycloalkyl, wherein the $C_{1-3}$ alkyl, $C_{1-3}$ alkoxy and $C_{3-6}$ cycloalkyl are each independently optionally substituted with 1, 2 or 3 $R_c$;

n is selected from 0, 1 and 2; and $R_a$, $R_b$ and $R_c$ are each independently selected from H, F, Cl, Br, I, $NH_2$ and OH.

2. The compound according to claim 1 or a pharmaceutically acceptable salt thereof, wherein $R_1$ and $R_2$ are each independently selected from H, OH, F and $CH_3$, wherein the $CH_3$ is optionally substituted with 1, 2 or 3 F.

3. The compound according to claim 2 or a pharmaceutically acceptable salt thereof, wherein $R_1$ and $R_2$ are each H.

4. The compound according to claim 1 or a pharmaceutically acceptable salt thereof, wherein $R_1$ and $R_2$ are taken together with the atom to which they are commonly attached to form a cyclopropyl, cyclobutyl, cyclopentyl, oxetanyl or azetidinyl, wherein the cyclopropyl, cyclobutyl, cyclopentyl, oxetanyl or azetidinyl is optionally substituted with 1, 2 or 3 F.

5. The compound according to claim 4 or a pharmaceutically acceptable salt thereof, wherein $R_1$ and $R_2$ are taken together with the atom to which they are commonly attached to form a

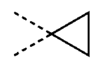

6. The compound according to claim 1 or a pharmaceutically acceptable salt thereof, wherein $R_3$, $R_4$, $R_5$ and $R_6$ are each independently selected from H and F.

7. The compound according to claim 6 or a pharmaceutically acceptable salt thereof, wherein the structural moiety

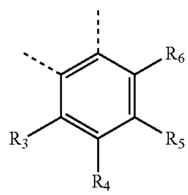

is selected from

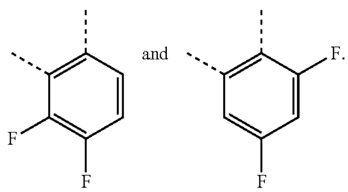

8. The compound according to claim 1 or a pharmaceutically acceptable salt thereof, wherein $R_7$, $R_8$ and $R_9$ are each independently selected from H and F.

9. The compound according to claim 8 or a pharmaceutically acceptable salt thereof, wherein the structural moiety

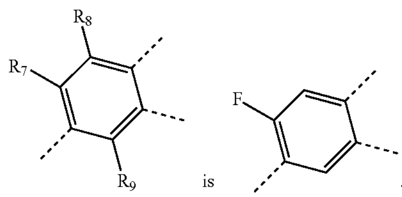

10. The compound according to claim 1 or a pharmaceutically acceptable salt thereof, wherein $L_3$ and $L_4$ are each O.

11. The compound according to claim 1 or a pharmaceutically acceptable salt thereof, wherein n is selected from 1 and 2.

12. The compound according to claim 1 or a pharmaceutically acceptable salt thereof, wherein the structural moiety

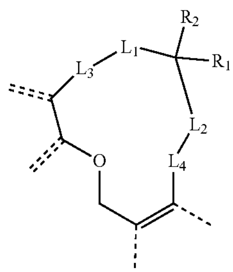

is selected from

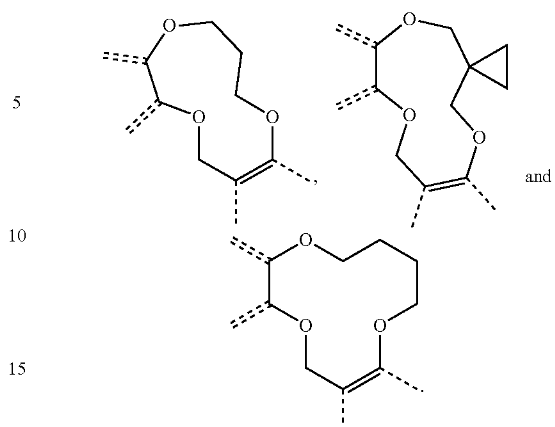

13. The compound according to claim 1, or a pharmaceutically acceptable salt thereof, wherein the compound is of formula (I-1):

(I-1)

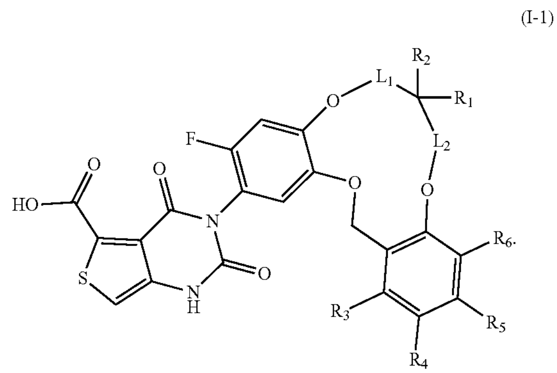

14. The compound according to claim 1, or a pharmaceutically acceptable salt thereof, wherein the compound is of formula (I):

(I)

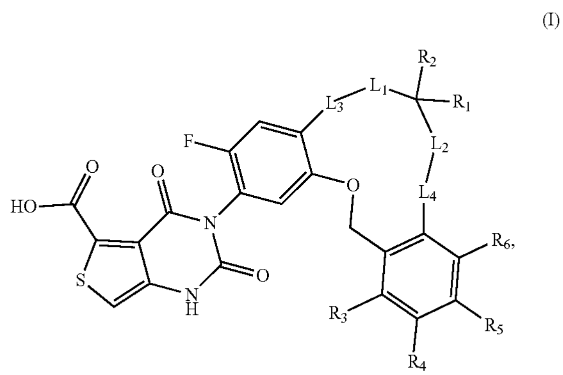

wherein $L_1$ and $L_2$ are each independently selected from $-(CH_2)_n-$;

$L_3$ and $L_4$ are each independently selected from $-CH_2-$, $-CH{=}CH-$, $-O-$ and $-S-$;

$R_1$ and $R_2$ are each independently selected from H, OH, F, Cl, $C_{1-3}$ alkyl and $C_{1-3}$ alkoxy, wherein the $C_{1-3}$ alkyl and $C_{1-3}$ alkoxy are each independently optionally substituted with 1, 2 or 3 $R_a$;

alternatively, $R_1$ and $R_2$ are taken together with the atom to which they are commonly attached to form a $C_{3-6}$ cycloalkyl or 4- to 6-membered heterocycloalkyl, wherein the $C_{3-6}$ cycloalkyl or 4- to 6-membered heterocycloalkyl is optionally substituted with 1, 2 or 3 $R_b$;

$R_3$, $R_4$, $R_5$ and $R_6$ are each independently selected from H, F, Cl, Br and I;

n is selected from 0, 1 and 2;

$R_a$ and $R_b$ are each independently selected from H, F, Cl, Br, and I; and the "4- to 6-membered heterocycloalkyl" comprises 1, 2 or 3 heteroatoms selected from N, NH, O and S.

15. A compound as shown below, or a pharmaceutically acceptable salt thereof,

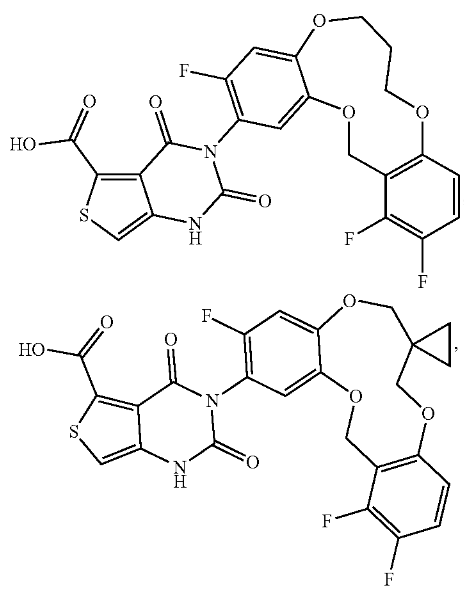

-continued

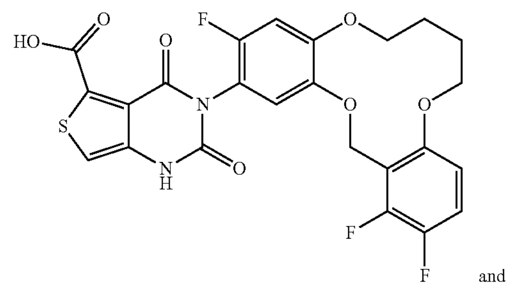

and

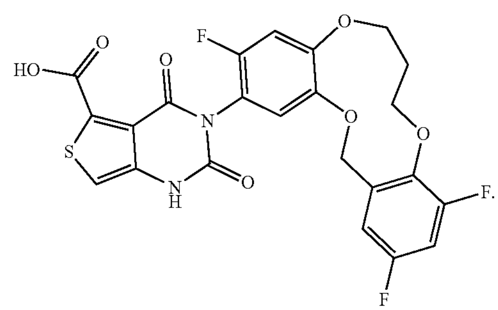

16. A method of treating a disease related to a GnRH receptor in a subject in need thereof, comprising administering to the subject Use of the compound according to claim 1, or a pharmaceutically acceptable salt thereof, wherein the disease related to a GnRH receptor is endometriosis and/or uterine fibroids.

* * * * *